United States Patent
Tsunomori et al.

(10) Patent No.: US 9,483,684 B2
(45) Date of Patent: Nov. 1, 2016

(54) MEDICAL IMAGE PROCESSOR AND STORAGE MEDIUM

(71) Applicants: Konica Minolta, Inc., Tokyo (JP); Tohoku University, Sendai-shi, Miyagi (JP)

(72) Inventors: Akinori Tsunomori, Tokyo (JP); Hisatake Okada, Tokyo (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/387,405

(22) PCT Filed: Mar. 27, 2013

(86) PCT No.: PCT/JP2013/058917
§ 371 (c)(1),
(2) Date: Sep. 23, 2014

(87) PCT Pub. No.: WO2013/146841
PCT Pub. Date: Oct. 3, 2013

(65) Prior Publication Data
US 2015/0049936 A1 Feb. 19, 2015

(30) Foreign Application Priority Data
Mar. 30, 2012 (JP) .................. 2012-078717

(51) Int. Cl.
*G06K 9/00* (2006.01)
*G01N 21/64* (2006.01)
(Continued)

(52) U.S. Cl.
CPC ......... *G06K 9/0014* (2013.01); *G01N 21/6456* (2013.01); *G06K 9/4661* (2013.01);
(Continued)

(58) Field of Classification Search
USPC ........................................................ 382/133
See application file for complete search history.

(56) References Cited

U.S. PATENT DOCUMENTS

| 8,428,331 B2* | 4/2013 | DiMarzio | G02B 21/0004 382/133 |
| 2002/0081014 A1* | 6/2002 | Ravkin | G01N 15/1475 382/134 |

(Continued)

FOREIGN PATENT DOCUMENTS

| JP | 200477389 | 3/2004 |
| JP | 2007074722 | 7/2007 |

(Continued)

OTHER PUBLICATIONS

Brügmann, Anja, et al. "Digital image analysis of membrane connectivity is a robust measure of HER2 immunostains." Breast cancer research and treatment 132.1 (2012): 41-49.*

(Continued)

*Primary Examiner* — Siamak Harandi
*Assistant Examiner* — Sean Conner
(74) *Attorney, Agent, or Firm* — Lucas & Mercanti, LLP

(57) ABSTRACT

A medical image processor and storage medium are shown. According to one implementation, a medical image processor includes an input unit, an operation unit, a cell nucleus extracting unit, a fluorescent bright point extracting unit, a feature amount calculating unit, and an output unit. The input unit is used to input a cell shape image showing a shape of a cell and a fluorescent image showing expression of a specific protein as a fluorescent bright point. The operation unit is used to specify an analysis target region. The cell nucleus extracting unit extracts a region of a cell nucleus. The fluorescent bright point extracting unit extracts a fluorescent bright point. The feature amount calculating unit calculates a feature amount showing an expression amount of the specific protein. The output unit outputs the calculated feature amount.

6 Claims, 20 Drawing Sheets

(51) Int. Cl.
*G06K 9/46* (2006.01)
*G06T 7/00* (2006.01)

(52) U.S. Cl.
CPC ......... *G06T7/0012* (2013.01); *G01N 21/6458* (2013.01); *G06T 2207/10064* (2013.01); *G06T 2207/20021* (2013.01); *G06T 2207/20104* (2013.01); *G06T 2207/20221* (2013.01); *G06T 2207/30024* (2013.01); *G06T 2207/30096* (2013.01)

(56) References Cited

U.S. PATENT DOCUMENTS

| | | | | |
|---|---|---|---|---|
| 2003/0231791 | A1* | 12/2003 | Torre-Bueno | G01N 21/6428 382/133 |
| 2005/0163359 | A1* | 7/2005 | Murao | G01N 15/1475 382/128 |
| 2005/0265588 | A1* | 12/2005 | Gholap | G06K 9/00127 382/128 |
| 2007/0219769 | A1* | 9/2007 | Herzog | G06K 9/0014 703/11 |
| 2007/0276230 | A1* | 11/2007 | Miwa | A61B 5/0059 600/431 |
| 2008/0032325 | A1* | 2/2008 | DiMarzio | G02B 21/18 435/29 |
| 2008/0212866 | A1* | 9/2008 | Lett | G01N 21/6428 382/133 |
| 2008/0240539 | A1* | 10/2008 | George | G01N 21/47 382/133 |
| 2009/0116724 | A1* | 5/2009 | Yamashita | G06K 9/00127 382/133 |
| 2009/0142274 | A1* | 6/2009 | Clark | B82Y 5/00 424/9.6 |
| 2009/0196482 | A1* | 8/2009 | Kobayashi | G01N 21/6458 382/133 |
| 2010/0290692 | A1* | 11/2010 | Macaulay | G06T 7/0012 382/133 |
| 2011/0211741 | A1* | 9/2011 | Nakano | G01N 15/1434 382/128 |
| 2011/0249883 | A1* | 10/2011 | Can | G06K 9/0014 382/133 |

FOREIGN PATENT DOCUMENTS

| | | |
|---|---|---|
| JP | 2009-115599 A | 5/2009 |
| JP | 2009-265067 | 11/2009 |
| JP | 2010-19656 A | 1/2010 |
| WO | WO2009/110614 A1 | 9/2009 |
| WO | 2012029342 | 3/2012 |
| WO | WO2012/039219 A1 | 3/2012 |

OTHER PUBLICATIONS

Jiang, Shan, Muthu Kumara Gnanasammandhan, and Yong Zhang. "Optical imaging-guided cancer therapy with fluorescent nanoparticles." Journal of the Royal Society Interface 7.42 (2010): 3-18.*

Chen, Chuang, et al. "Quantum dots-based immunofluorescence technology for the quantitative determination of HER2 expression in breast cancer." Biomaterials 30.15 (2009): 2912-2918.*

Gao, Xiaohu, et al. "In vivo cancer targeting and imaging with semiconductor quantum dots." Nature biotechnology 22.8 (2004): 969-976.*

English translation of the International Preliminary report on patentability (Written Opinion) dated May 28, 2013.

Office Action dated Sep. 15, 2015 issued from the corresponding Japanese patent application No. 2014-507942.

English translation of Office Action dated Sep. 15, 2015 issued from the corresponding Japanese patent application No. 2014-507942.

European Search Report; Date, Nov. 10, 2015; Application No. 13767991.6-1906 / 2833123; Applicant, Konica Minolta, Inc.; Total of 6 pages.

T Gaiser: "Automated analysis of protein expression and gene amplification within the same cells of paraffin-embedded tumour tissue", Analytical Cellular Pathology / Cellular Oncology, vol. 33, Jan. 1, 2010 (Jan. 1, 2010), pp. 105-112, XP55066405, DOI: 10.3233/ACP-CL0-2010-0532 * abstract; figures 2,3* ' * section 1. Introduction *.

* cited by examiner

MEDICAL IMAGE PROCESSOR AND STORAGE MEDIUM

CROSS REFERENCE TO RELATED APPLICATIONS

This application is a 371 of PCT/JP2013/058917 filed on Mar. 27, 2013 which, in turn, claimed the priority of Japanese Patent Application No. JP2012-078717 filed on Mar. 30, 2012 both applications are incorporated herein by reference.

TECHNICAL FIELD

The present invention relates to a medical image processor and a program.

BACKGROUND ART

In pathological diagnosis, first, after processing of dehydrating the obtained tissue so as to be fixed and blocking with paraffin, the above is cut into thin pieces with a thickness of 2 to 8 μm, the paraffin is removed, and the above is stained to observe with a microscope. The pathologist performs diagnosis based on morphologic information such as change in size and shape of a nucleus of a cell, change in pattern as a tissue, etc., and stain information in the microscopic image. Methods known as the tissue staining method used in pathological diagnosis include a conventional chromatic staining method (for example, Hematoxylin and Eosin staining; hereinafter referred to as HE staining) and a chromatic staining method using enzyme (for example, DAB (diaminobenzidine) staining).

In pathological diagnosis, specifying the protein overexpressing in the tissue slice and its expression amount may be very important information for prognostic expectation and determining the future treatment plan.

For example, HER2 protein coding HER2 gene is a receptor type glycoprotein which penetrates the cell membrane, is composed of 3 domains which are extracellular, transmembrane, and intracellular, is activated by phosphorylating of tyrosine residue when bonded with a growth factor, and is said to be involved in proliferation and malignant alteration of cells through signaling pathways. Overexpression of HER2 protein can be seen in breast cancer, lung cancer, colon cancer, stomach cancer, bladder cancer, etc.

HER2 protein is considered to be a prognostic factor of breast cancer, and it is known that especially in a case where lymph node metastasis is positive, the prognosis of cases where HER2 is positive is significantly poor. HER2 protein is also gathering attention as an information factor for deciding adaptation of a molecularly targeted drug (trastuzumab) and as a result prediction factor of anticancer drugs such as anthracycline type, taxane type, etc.

Typically, overexpression of HER2 protein is examined by an immunohistochemical method (IHC method) and overexpression of HER2 gene is examined by FISH method. According to the HER examination guideline, first, positive, negative, boundary region is discriminated by a simple IHC method, and when the result is positive, it is decided that trastuzumab is provided. When the result is in the boundary region with the IHC method, further examination is done to discriminate positive and negative by the FISH method.

Comparing the IHC method and the FISH method, the IHC method is easier, but there is the problem that accuracy is low. Turning to the FISH method, the accuracy is high, but the process is troublesome, and the cost is high. In other words, there are needs for development of a method of an IHC method which has the same accuracy as the FISH method. Moreover, there are needs for development of a method where the dependence on the person is low and which can be automated.

For example, Patent Document 1 describes a system where a cell nucleus is extracted from an image of biological tissue stained by the DAB method, a cell membrane is specified from an image of biological tissue based on the cell nucleus, a stained state of a cell membrane is determined, and expression of HER2 protein is evaluated based on the result of determination.

PRIOR ART DOCUMENT

Patent Document

Patent Document 1: Japanese Patent Application Laid-Open Publication No. 2009-115599

DISCLOSURE OF THE INVENTION

Problems to be Solved by the Invention

However, in the DAB method, there is increase due to the enzyme and the method lacks quantitative capabilities. Therefore, according to the technique described in patent document 1, it is not possible to find a quantitative expression amount of the HER2 protein. Moreover, the cell membrane does not maintain a certain shape in an invasive portion, and analysis by specifying the cell membrane is difficult.

The problem to be solved by the present invention is to enable a physician to quantitatively understand an expression amount of a specific protein in a tissue slice.

Means for Solving the Problem

In order to solve the above problems, according to a first aspect of the present invention, there is provided a medical image processor including:

an input unit to input a cell shape image showing a shape of a cell in a tissue slice and a fluorescent image showing expression of a specific protein in the tissue slice as a fluorescent bright point;

an operation unit to specify an analysis target region from the cell shape image;

a cell nucleus extracting unit which extracts a region of a cell nucleus from the cell shape image;

a fluorescent bright point extracting unit which extracts a fluorescent bright point showing expression of the specific protein from the fluorescent image;

a feature amount calculating unit which calculates a feature amount showing an expression amount of the specific protein in the specified analysis target region based on the extracted cell nucleus region in the analysis target region specified with the operation unit and the fluorescent bright point; and an output unit which outputs the calculated feature amount.

Preferably, in the medical image processor, the feature amount calculating unit obtains information of a number of fluorescent bright points and a number of cell nuclei in the analysis target region specified with the operation unit, and based on the obtained number of cell nuclei and the number of fluorescent bright points, the feature amount calculating unit calculates the feature amount showing the expression amount of the specific protein in the specified analysis target region.

Preferably, in the medical image processor, the feature amount calculating unit calculates a number of the fluorescent bright points in each cell nucleus in the specified analysis target region as the feature amount showing the expression amount of the specific protein.

Preferably, the medical image processor further includes, a synthesis image generating unit which generates a synthesis image of the cell shape image and the fluorescent image, wherein, the output unit outputs the synthesis image overlapped with an annotation showing a position of the analysis target region specified with the operation unit together with the feature amount.

Preferably, in the medical image processor, the cell shape image and the fluorescent image compose one image which show the shape of the cell in the tissue slice and the expression of the specific protein in the tissue slice as the fluorescent bright point.

According to a second aspect of the present invention, there is provided a program for controlling a computer to function as:

an input unit to input a cell shape image showing a shape of a cell in a tissue slice and a fluorescent image showing expression of a specific protein in the tissue slice as a fluorescent bright point;

an operation unit to specify an analysis target region from the cell shape image;

a cell nucleus extracting unit which extracts a region of a cell nucleus from the cell shape image;

a fluorescent bright point extracting unit which extracts a fluorescent bright point showing expression of the specific protein from the fluorescent image;

a feature amount calculating unit which calculates a feature amount showing an expression amount of the specific protein in the specified analysis target region based on the extracted cell nucleus region in the analysis target region specified with the operation unit and the fluorescent bright point; and an output unit which outputs the calculated feature amount.

Advantageous Effect of the Invention

According to the present invention, a physician is able to quantitatively understand an expression amount of a specific protein in a tissue slice, and with this, prognostic expectation and determining the future treatment plan becomes easier.

EMBODIMENT FOR CARRYING OUT THE INVENTION

Embodiments of the present invention are described below with reference to the drawings, however, the present invention is not limited to the illustrated examples.

—First Embodiment—

<Configuration of Pathological Diagnosis Assistance System 100>

Figure 1:
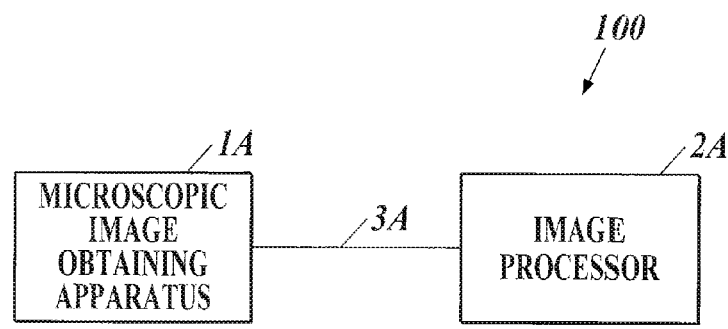
FIG. 1 is a diagram showing a system configuration of a pathological diagnosis assistance system.

FIG. 1 shows an example of an entire configuration of a pathological diagnosis assistance system 100 of the first embodiment. The pathological diagnostic assistance system 100 obtains a microscopic image of a tissue slice of a human body stained with a predetermined staining reagent, and outputs a feature amount quantitatively expressing a specific biological substance in the tissue slice of the observation target by analyzing the obtained microscopic image.

As shown in FIG. 1, the pathological diagnosis assistance system 100 includes a microscopic image obtaining apparatus 1A and an image processor 2A connected to each other through an interface such as a cable 3A so as to be able to transmit and receive data. The method of connecting the microscopic image obtaining apparatus 1A and the image processor 2A is not limited. For example, the microscopic image obtaining apparatus 1A and the image processor 2A can be connected by a LAN (Local Area Network) or can be connected wirelessly.

The microscopic image obtaining apparatus 1A is a well-known optical microscope with a camera. The microscopic image obtaining apparatus 1A obtains the microscopic image of the tissue piece on the slide placed on a slide fixing stage, and transmits the image to the image processor 2A.

The microscopic image obtaining apparatus 1A includes an irradiating unit, an image forming unit, an imaging unit, a communication I/F, etc. The irradiating unit includes a light source, filter, etc., which irradiates light on the tissue slice on the slide placed on the slide fixing stage. The image forming unit includes an ocular lens, an object lens, etc., and forms an image of transmitted light, reflected light, or fluorescence light from the tissue slice on the slide due to the irradiated light. The imaging unit is a camera provided in a microscope which includes a CCD (Charge Coupled Device) sensor, etc., and images an image formed on an image forming face by the image forming unit to generate digital image data (R, G, B image data) of the microscopic image. The communication I/F transmits the generated image data of the microscopic image to the image processor 2A. According to the present embodiment, the microscopic image obtaining apparatus 1A includes a bright field unit combining the irradiating unit and the image forming unit suitable for bright field observation and a fluorescent unit combining the irradiating unit and the image forming unit suitable for fluorescent observation. The bright field/fluorescence can be switched by switching the units.

The microscopic image obtaining apparatus 1A is not limited to a microscope with a camera. For example, a virtual microscope slide creating apparatus which scans a slide on a slide fixing stage of a microscope and obtains a microscopic image of the entire tissue slice can be used (for example, see Japanese Patent Application Laid-Open Publication No. 2002-514319). According to the virtual microscope slide creating apparatus, image data with which the entire image of the tissue slice on the slide can be viewed at once on the display section can be obtained.

The image processor 2A is a medical image processor which analyzes the microscopic image transmitted from the microscopic image obtaining apparatus 1A, calculates the feature amount which quantitatively shows the expression amount of a certain biological substance in the tissue slice of the observation target, and outputs the calculated feature amount.

Figure 2:
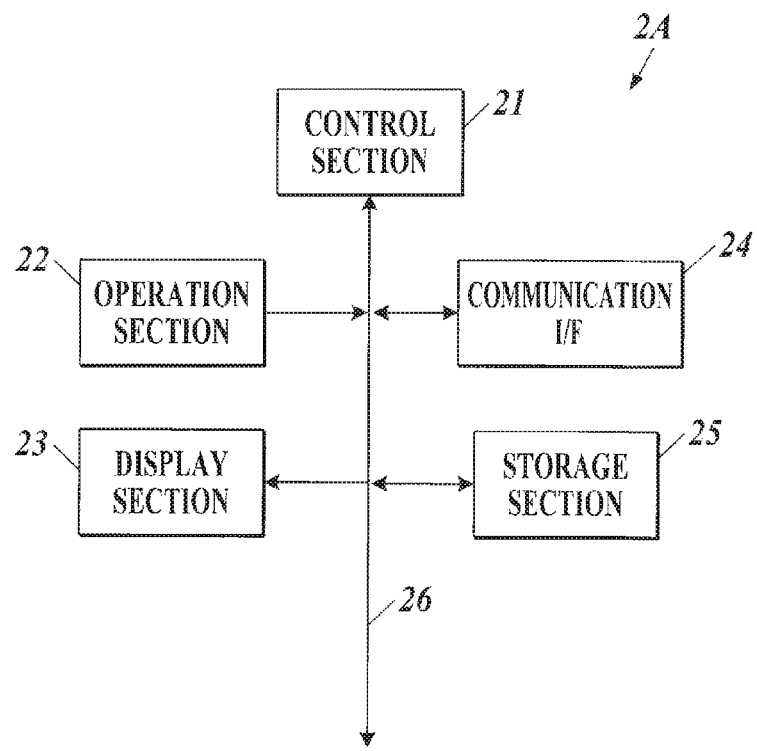
FIG. 2 is a block diagram showing a functional configuration of an image processor of FIG. 1.

FIG. 2 shows an example of a functional configuration of the image processor 2A. As shown in FIG. 2, the image processor 2A includes a control section 21, an operation section 22, a display section 23, a communication I/F 24, a storage section 25, and the like, and each section is connected through a bus 26.

The control section 21 includes a CPU (Central Processing Unit), a RAM (Random Access Memory), and the like, performs various processing in coordination with various programs stored in the storage section 25, and collectively controls the operation of the image processor 2A. For example, the control section 21 performs image analysis processing A (see FIG. 10) in coordination with a program stored in the storage section 25, and realizes functions as a cell nucleus extracting unit, fluorescent bright point extracting unit, feature amount calculating unit, and synthesized image generating unit.

The operating section 22 includes a keyboard provided with character input keys, numeric input keys and various function keys and a pointing device such as a mouse, and outputs pressed signals of the keys pressed on the keyboard and operation signals of the mouse, and outputs the signals as the input signal to the control section 21.

The display section 23 includes a monitor such as a CRT (Cathode Ray Tube), LCD (Liquid Crystal Display), etc., and displays various screens according to an instruction of a display signal input from the control section 21. According to the present embodiment, the display section 23 functions as an output unit to output the calculated feature amount.

The communication I/F 24 is an interface for transmitting and receiving data with external devices such as the microscopic image obtaining apparatus 1A. According to the present embodiment, the communication I/F 24 functions as an input unit.

The storage section 25 includes, for example, an HDD (Hard Disk Drive), a nonvolatile semiconductor memory, etc. The storage section 25 stores various programs and various pieces of data as described above.

Other than the above, the image processor 2A can include a LAN adaptor, a router, etc., and can be connected to external devices through a communication network such as a LAN.

The image processor 2A of the first embodiment analyses the bright field image (HE stain image) and the fluorescent image transmitted from the microscopic image obtaining apparatus 1A.

Figure 3:
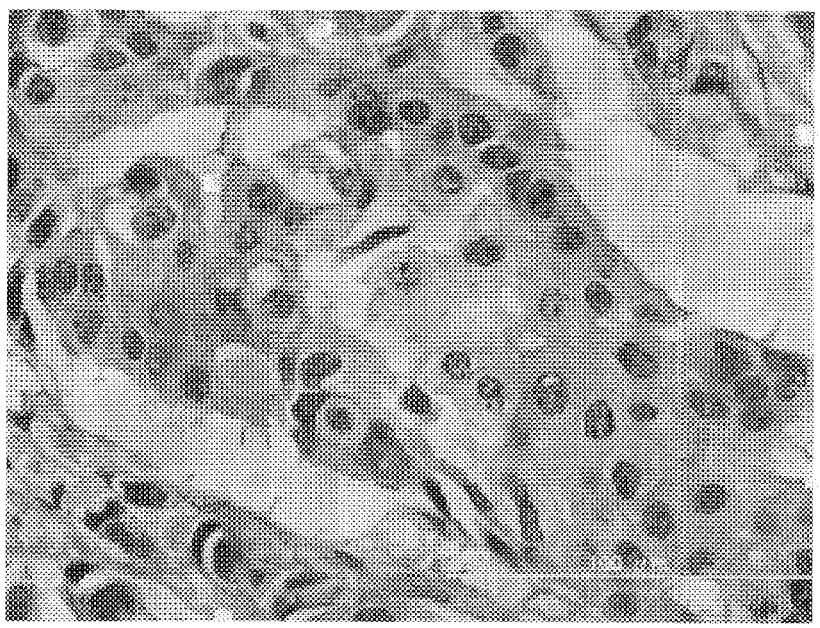
FIG. 3 is a diagram showing an example of a bright field image.

The bright field image is a microscopic image obtained by forming an enlarged image of a tissue slice with HE (hematoxylin-eosin) stain in a bright field in the microscopic image obtaining apparatus 1A and capturing the image. Hematoxylin is a blue purple dye and stains the cell nucleus, bone tissue, a portion of cartilage tissue, serous fluid component etc. (basophilic tissue, etc.). Eosin is a red to pink dye and stains cytoplasm, connective tissue of soft tissue, red blood cell, fibrin, endocrine granule, etc. (eosinophilic tissue, etc.). FIG. 3 shows an example of a bright field image capturing the tissue slice with HE stain. As shown in FIG. 3, in the bright field image capturing the tissue slice with the HE stain, the shape of the cell in the tissue slice appears. The cell nucleus is shown with a darker color than the surrounding cytoplasm (blue purple color) to be distinguished from the surrounding portion, and in the bright field image, it is possible to clearly see the shape of the cell nucleus.

Figure 4:
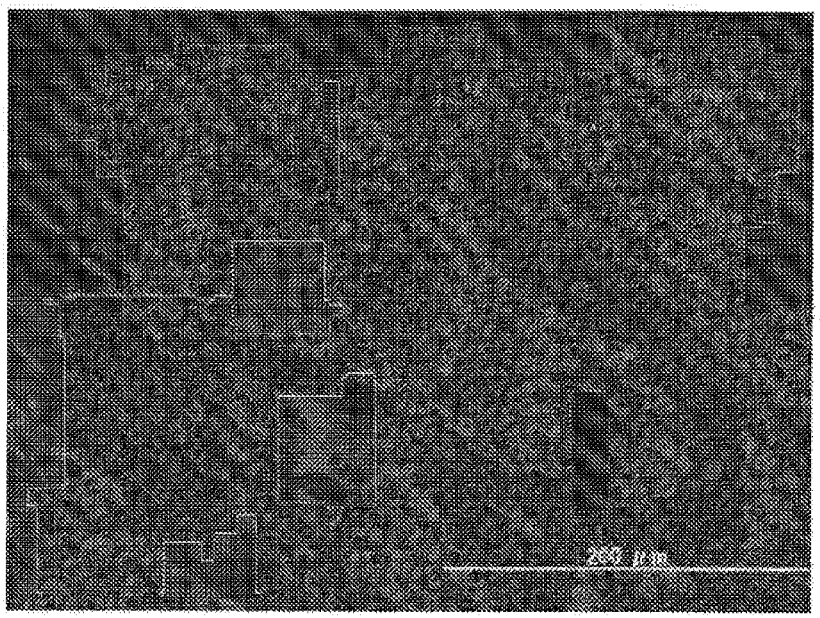
FIG. 4 is a diagram showing an example of a fluorescent image.

A fluorescent image is a microscopic image obtained by irradiating excitation light with a predetermined wavelength in the microscopic image obtaining apparatus 1A on the tissue slice stained using staining reagent including a nanoparticle including a fluorescent substance which specifically bonds with a certain biological substance and/or which bonds with reactive biological substance recognition site (hereinafter called fluorescent substance included nanoparticle) so that the fluorescent substance included nanoparticle emits light (fluorescence), and forming an image with the fluorescence to capture the image. In other words, the fluorescence which appears in the fluorescent image shows expression of the certain biological substance corresponding to the biological substance recognition site in the tissue slice. FIG. 4 shows an example of a fluorescent image.

<Obtaining Fluorescent Image>

Here, the method of obtaining the fluorescent image is described in detail including the description of the staining reagent used when obtaining the fluorescent image (fluorescent substance included nanoparticle), staining method of the tissue slice with the staining reagent, etc.

[Fluorescent Substance]

Examples of the fluorescent substance used in the staining reagent to obtain the fluorescent image include, fluorescent organic dye and quantum dot (semiconductor particle). Preferably, the substance shows an emission of visible rays to near infrared rays with a wavelength within the range of 400 to 1100 nm when excited by ultraviolet rays to near infrared rays with a wavelength within the range of 200 to 700 nm.

Examples of fluorescent organic dye include, fluorescein type dye molecule, rhodamine type dye molecule, Alexa Fluor (Invitrogen) type dye molecule, BODIPY (Invitrogen) type dye molecule, cascade type dye molecule, coumarin type dye molecule, eosin type dye molecule, NBD type dye molecule, pyrene type dye molecule, Texas Red type dye molecule, cyanine type dye molecule, and the like.

Specific examples include, 5-carboxy-fluorescein, 6-carboxy-fluorescein, 5,6-dicarboxy-fluorescein, 6-carboxy-2',4,4',5',7,7'-hexachlorofluorescein, 6-carboxy-2',4, 7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (the above, Invitrogen), methoxycoumalin, eosin, NBD, pyrene, Cy5, Cy5.5, Cy7, etc. The above can be used alone or by mixing a plurality of types.

Examples of quantum dots which can be used include quantum dots including the following as the component, II-VI compounds, III-V compounds or IV element (also called, "II-VI quantum dot", "III-V quantum dot", "IV quantum dot", respectively). The above can be used alone or by mixing a plurality of types.

Specific examples include, but are not limited to, CdSe, CdS, CdTe, ZnSe, ZnS, ZnTe, InP, InN, InAs, InGaP, GaP, GaAs, Si, and Ge.

A quantum dot with the above quantum dot as the core and a shell provided on the core can also be used. As a method of expressing the quantum dot including a shell in the present specification, when the core is CdSe and the shell is ZnS, the above is expressed as CdSe/ZnS. Examples which can be used include, but are not limited to, CdSe/ZnS, CdS/ZnS, InP/ZnS, InGaP/ZnS, Si/SiO$_2$, Si/ZnS, Ge/GeO$_2$, Ge/ZnS, etc.

The quantum dot in which the surface is processed with organic polymer, etc. can be used as necessary. Examples include CdSe/ZnS with surface carboxy group (Invitrogen), CdSe/ZnS with surface amino group (Invitrogen), etc.

[Fluorescent Substance Included Nanoparticle]

The fluorescent substance included nanoparticle of the present embodiment is a nanoparticle with the fluorescent substance dispersed inside, and the fluorescent substance and the nanoparticle itself can be chemically bonded or not bonded.

The material composing the nanoparticle is not limited and examples include polystyrene, polyactate, silica, and the like.

The fluorescent substance included nanoparticle used in the present embodiment can be made by well-known methods. For example, a silica nanoparticle including fluorescent organic dye can be synthesized by referring to synthesizing an FTIC included silica particle as described in Langmuir volume 8, page 2921 (1992). Various fluorescent organic dye included silica nanoparticles can be synthesized using a desired fluorescent organic dye instead of FITC.

The silica nanoparticle including the quantum dot can be synthesized by referring to synthesizing of the CdTe included silica nanoparticle as described in New Journal of Chemistry, Volume 33, page 561 (2009).

The polystyrene nanoparticle including the fluorescent organic dye can be made using the copolymerization method using the organic dye including polymerizable functional group as described in U.S. Pat. No. 4,326,008 (1982), and impregnating method of the fluorescent organic dye to the polystyrene nanoparticle as described in U.S. Pat. No. 5,326,692 (1992).

The polymer nanoparticle including the quantum dot can be made using the impregnating method of the quantum dot to the polystyrene nanoparticle as described in Nature Biotechnology Volume 19, page 631 (2001).

The average particle diameter of the fluorescent substance included nanoparticle used in the present embodiment is not limited, and the fluorescent substance included nanoparticle with an average particle diameter with about 30 to 800 nm can be used. The variation coefficient showing the variety of the particle diameter (=(typical deviation/average value)×100%) is not limited, and preferably, the value is 20% or less. The electronic microscopic picture is captured using the scanning electron microscope (SEM), and the cross sectional area of a sufficient number of particles is measured. The diameter of the circle when each measurement value is to be the area of the circle is obtained as the particle diameter. According to the present embodiment, the calculated average of the particle diameter of 1000 particles is to be the average particle diameter. The variation coefficient is to be a value calculated from the particle diameter distribution of 1000 particles.

[Bonding of the Biological Substance Recognition Site and Fluorescent Substance Included Nanoparticle]

The biological substance recognition site of the present embodiment is a site which specifically bonds and/or reacts with the target biological substance. The target biological substance is not limited as long as there is a substance which specifically bonds with the target biological substance. Representative examples includes protein (peptide), nucleic acid (oligonucleotide, polynucleotide), antibody, etc. Therefore, examples of substances which bond with such target biological substance include, antibody which recognizes the protein as antigen, other protein which specifically bonds with the protein, nucleic acid including a base sequence which hybrids with the nucleic acid, and the like. Specific examples include, anti HER2 antibody which specifically bonds with the HER2 which is a protein on the surface of the cell, anti ER antibody which specifically bonds with the estrogen receptor (ER) on the cell nucleus, anti actin antibody which specifically bonds with the actin forming the cytoskeleton, and the like. Among the above, anti HER2 antibody and anti ER antibody bonded to the fluorescent substance included nanoparticle are preferable because the above can be used in selecting medication for breast cancer.

The form of bonding between the biological substance recognition site and the fluorescent substance included nanoparticle is not limited, and examples include, covalent bonding, ion bonding, hydrogen bonding, coordinate bonding, physical adsorption, chemical adsorption, etc. Preferably, bonding with strong bonding force such as covalent bonding is preferable for stability of bonding.

Moreover, there can be an organic molecule which connects the biological substance recognition site with the fluorescent substance included nanoparticle. For example, in order to suppress non-specific adsorption with the biological substance, a polyethyleneglycol chain can be used and SM (PEG)12 by Thermo Scientific can be used.

When the biological substance recognition site is bonded to the fluorescent substance included silica nanoparticle, the same process can be applied whether the fluorescent substance is the fluorescent organic dye or the quantum dot. For example, a silane coupling agent which is a compound widely used for bonding inorganic material and organic material can be used. The silane coupling agent is a compound including an alkoxysilyl group providing a silanol group with hydrolysis in one end of the molecule and a functional group such as carboxy group, amino group, epoxy group, aldehyde group, etc. in the other end, and bonds with the inorganic material through an oxygen atom of the silanol group. Specific examples include, mercaptopropyl triethoxysilane, glycidoxypropyl triethoxysilane, aminopropyl triethoxysilane, silane coupling agent including polyethylene glycol chain (for example, PEG-silane no. SIM6492.7 by Gelest), and the like. When the silane coupling agent can be used, two or more types can be used together.

Well-known methods can be used as the reaction method between the fluorescent organic dye including silica nanoparticle and the silane coupling agent. For example, the obtained fluorescent organic dye included silica nanoparticle can be dispersed in pure water, the aminopropyl triethoxysilane can be added and the above can be reacted in room temperature for 12 hours. After the reaction ends, by centrifugal separation or filtration, it is possible to obtain a fluorescent organic dye included silica nanoparticle modified with the aminopropyl group. Next, the amino group is reacted with the carboxy group in the antibody so that the antibody can bond with the fluorescent organic dye included silica nanoparticle through amide bonding. According to necessity, condensing agent such as EDC (1-Ethyl-3-[3-Dimethylaminopropyl]carbodiimide Hydrochloride: Pierce (Registered Trademark)) can also be used.

According to necessity, a linker compound including a portion which can directly bond with the fluorescent organic dye included silica nanoparticle modified with the organic molecule and a portion which can bond with the molecule target substance can be used. For example, when sulfo-SMCC (Sulfosuccinimidyl 4[N-maleimidomethyl]-cyclohexane-1-carboxylate:Pierce) which has a portion which selectively reacts with the amino group and a portion which selectively reacts with the mercapto group is used, the amino group of the fluorescent organic dye included silica nanoparticle modified with aminopropyl triethoxysilane and the mercapto group in the antibody are bonded, and with this, the fluorescent organic dye included silica nanoparticle bonded with the antibody is made.

When the biological substance recognition site is bonded to the fluorescent substance included polystyrene nanoparticle, even if the fluorescent substance is the fluorescent organic dye, the same process as the quantum dot can be applied. In other words, by impregnating the fluorescent organic dye and the quantum dot in the polystyrene nanoparticle with the functional group such as the amino group, etc., it is possible to obtain the fluorescent substance included polystyrene nanoparticle with the functional group, and then by using the EDC or the sulfo-SMCC, the fluorescent substance included polystyrene nanoparticle bonded with the antibody is made.

Examples of the antibody which recognizes the specific antigen include the following, M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, C-MET, collagen type IV, Cox-2, cyclin D1, keratin, cytokeratin (high molecular mass), pankeratin, pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, VIII factor related antigen, fassin, FSH, galectin-3, gastrin, GFAP, glucagon, glycophorin A, granzyme B, hCG, hGH, helicobacter pyroli, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, p63, PAX 5, PLAP, pneumocystis calini, podoplanin (D2-40), PGR, prolactin, PSA, prostatic acid phosphatase, Renal Cell Carcinoma, S100, somatostatin, spectrin, synaptophysin, TAG-72, TdT, cycloglobulin, TSH, TTF-1, TRAcP, tryptase, villin, vimentin, WT1, Zap-70, and the like.

[Staining Method]

Below, a staining method of a tissue slice is described. The staining method described below is not limited to a pathological slice of tissue, and can be applied to staining cells.

The method of creating the slice to which the staining method described below can be applied is not limited, and the slice which is made by well-known methods can be used.

1) Removing Paraffin

A pathological slice is immersed in a container with xylene, and paraffin is removed. The temperature is not limited, and the processing can be performed at room temperature. Preferably, the immersing time is 3 minutes or more to 30 minutes or less. The xylene can be changed during the immersion as necessary.

Next, the pathological slice is immersed in a container with ethanol, and the xylene is removed. The temperature is not limited, and the processing can be performed at room temperature. Preferably, the immersing time is 3 minutes or more to 30 minutes or less. The ethanol can be changed during the immersion as necessary.

Next, the pathological slice is immersed in a container with water, and the ethanol is removed, The temperature is not limited, and the processing can be performed at room temperature. Preferably, the immersing time is 3 minutes or more to 30 minutes or less. The water can be changed during the immersion as necessary.

2) Activating Processing

Activating processing of the target biological substance is performed according to well-known methods. Although the activating conditions are not specifically set, examples of activating liquid that can be used include, 0.01M citric acid buffered solution (pH 6.0), 1 m MEDTA solution (pH 8.0), 5% urea, 0.1M tris-hydrochloric acid buffered solution. Examples of the heating device that can be used include autoclave, microwave, pressure pan, water bath, etc. The temperature is not limited, and the processing can be performed at room temperature. The processing can be performed at a temperature of 50 to 130° C. and the amount of time that the processing is performed can be 5 to 30 minutes.

Next, the slice after activating processing is immersed in the container with PBS (Phosphate Buffered Saline), and cleaning is performed. The temperature is not limited, and the processing can be performed at room temperature. Preferably, the immersing time is 3 minutes or more to 30 minutes or less. The PBS can be changed during the immersion as necessary.

3) Stain Using Fluorescent Substance Included Nanoparticle Bonded with Biological Substance Recognition Site The PBS dispersion liquid of the fluorescent substance included nanoparticle bonded with the biological substance recognition site is placed on the pathological slice and reacted with the target biological substance. By changing the biological substance recognition site bonded with the fluorescent substance included nanoparticle, staining can be applied to various biological substances. When the fluorescent substance included nanoparticle bonded with plural types of biological substance recognition sites is used, the fluorescent substance included nanoparticle PBS dispersion liquid of each of the above can be mixed in advance, or the liquid can be sequentially placed on the pathological slice separately.

The temperature is not limited, and the processing can be performed at room temperature. Preferably, the reacting time is 30 minutes or more to 24 hours or less.

Preferably, a well-known blocking agent such as BSA included PBS, etc. is dropped before staining with the fluorescent substance included nanoparticle.

Next, the slice after staining is immersed in the container with PBS, and the unreacted fluorescent substance included nanoparticle is removed. The temperature is not limited, and the processing can be performed at room temperature. Preferably, the immersing time is 3 minutes or more to 30 minutes or less. The PBS can be changed during the immersion as necessary. A cover glass is placed on the slice to be sealed. A commercially available sealing agent can be used as necessary.

When HE staining is performed, the HE staining is performed before sealing with the cover glass.

[Obtaining Fluorescent Image]

The microscopic image obtaining apparatus 1A is used on the stained pathological slice to obtain the microscopic image (fluorescent image) with a wide field. In the microscopic image obtaining apparatus 1A, the excitation light source and the fluorescence detecting optical filter are selected corresponding to the absorption maximum wavelength and the fluorescent wavelength of the fluorescent substance used in the staining reagent.

Preferably, the field of the fluorescent image is 3 $mm^2$ or more, more preferably 30 $mm^2$ or more, and even more preferably 300 $mm^2$ or more.

<Relationship Between Fluorescent Bright Point and FISH Score>

Here, as described below, the applicants made a Cy5 included silica nanoparticle (hereinafter referred to as nanoparticle 1) as one embodiment, and an indicator material A bonded with an anti HER2 antibody against the nanoparticle 1. Moreover, a CdSe/ZnS included silica nanoparticle (hereinafter referred to as nanoparticle 2) is made and an indicator material B bonded with an anti HER2 antibody is made with a nanoparticle 2. By using the made indicator material A and B and the indicator material C and D as the comparison example, an adjacent slice of the human breast tissue in which the FISH score is measured in advance is used to perform immunostaining, a plurality of fluorescent images with different fields are obtained, and the fluorescent bright spot appearing in each fluorescent image is measured to perform an experiment of finding the relation with the FISH score.

[Synthesis of Fluorescent Substance Included Nanoparticle]

Synthesis Example 1

Fluorescent Organic Dye Included Silica: Synthesis of Cy5 Included Silica Nanoparticle The Cy5 included silica nanoparticle (nanoparticle 1) is made by the method including the following steps of (1) to (5).

step (1): 1 mg (0.00126 mmol) of N-hydroxysuccinimideester derivative of Cy5 (GE healthcare) and 400 µL (1.796 mmol) of tetraethoxysilane are mixed.

step (2): 40 mL of ethanol and 10 mL of 14% aqueous ammonium are mixed.

step (3): The mixed liquid prepared in step (1) is added while stirring the mixed liquid made in step (2) at room temperature. The stirring continues for 12 hours from when the adding starts.

step (4): Centrifugal separation is performed on the reacted mixture at 10000 G for 60 minutes and the supernatant is removed.

step (5): Ethanol is added, precipitate is dispersed and centrifugal separation is performed again. Cleaning is performed using ethanol and pure water, one time each with the similar process.

The obtained nanoparticle 1 observed with the scanning electron microscope (SEM; Hitachi (registered trademark) S-800 type) has an average particle diameter of 110 nm, and a variation coefficient of 12%.

Synthesis Example 2

Quantum Dot Included Silica Synthesis of CdSe/ZnS Included Silica Nanoparticle with Emission Wavelength of 655 nm The CdSe/ZnS included silica nanoparticle (hereinafter referred to as nanoparticle 2) is made by the method including the following steps (1) to (5).

step (1): 10 µL of CdSe/ZnS decane dispersion liquid (Invitrogen, Qdot 655) and 40 µL of tetraethoxysilane are mixed.

step (2): 4 mL of ethanol and 1 mL of 14% aqueous ammonium are mixed.

step (3): The mixed liquid made in step (1) is added while stirring the mixed liquid made in step (2) at room temperature. The stirring continues for 12 hours from when the adding starts.

step (4): Centrifugal separation is performed on the reacted mixture at 10000 G for 60 minutes and the supernatant is removed.

step (5): Ethanol is added, precipitate is dispersed and centrifugal separation is performed again. Cleaning is performed using ethanol and pure water, one time each with the similar process.

The obtained nanoparticle 2 observed with the scanning electron microscope has an average particle diameter of 130 nm, and a variation coefficient of 13%.

[Bonding Antibody to Fluorescent Substance Included Silica Nanoparticle]

The antibody is bonded to the fluorescent substance included silica nanoparticle according to the method including the following steps (1) to (12). Here, an example using the nanoparticle 1 is shown, however, the same applies to the nanoparticle 2.

step (1): 1 mg of the nanoparticle 1 is dispersed in 5 mL of pure water. Next, 100 μL of aminopropyltriethoxysilane aqueous dispersion liquid is added and the stirring continues for 12 hours at room temperature.

step (2): Centrifugal separation is performed on the reacted mixture at 10000 G for 60 minutes and the supernatant is removed.

step (3): Ethanol is added, precipitate is dispersed and centrifugal separation is performed again. Cleaning is performed using ethanol and pure water, one time each with the similar process.

When the FT-IR measurement of the obtained silica nanoparticle modified with the amino group is performed, adsorption due to the amino group can be observed, and it is possible to confirm that the silica nanoparticle is modified with the amino group.

step (4): the silica nanoparticle modified with the amino group obtained in step (3) is adjusted to 3 nM using the PBS including 2 mM of EDTA (ethylenediaminetetraacetic acid).

step (5): SM(PEG) 12 (Thermoscientific, succinimidyl-[(N-maleomidopropionamid)-dodecaethyleneglycol]ester) is mixed in the solution adjusted in step (4) so that the final concentration is 10 mM and the above is reacted for 1 hour.

step (6): Centrifugal separation is performed on the reacted mixture at 10000 G for 60 minutes and the supernatant is removed.

step (7): PBS including 2 mM of EDTA is added, precipitate is dispersed and centrifugal separation is performed again. Cleaning by similar processing is performed 3 times. Finally, 50 μL of PBS is used to disperse again.

step (8): 100 μg of the anti HER2 antibody is dissolved in 100 μL of the PBS, 1M dithiothreitol (DTT) is added and the above is reacted for 30 minutes.

step (9): The excessive DTT is removed from the reacted mixture with the gel filter column and a reduced anti HER2 antibody solution is obtained.

step (10): The particle dispersion liquid obtained in step (7) with the nanoparticle 1 as the starting material is mixed with the reduced anti HER2 antibody solution obtained in step (9) in the PBS and the above is reacted for 1 hour.

step (11): 4 μL of 10 mM mercaptoethanol is added and the reaction is terminated.

step (12): Centrifugal separation is performed on the reacted mixture at 10000 G for 60 minutes and the supernatant is removed. Then, PBS including 2 mM of EDTA is added, the precipitate is dispersed and centrifugal separation is performed again. Cleaning by similar processing is performed 3 times. Finally, 500 μL of PBS is used to disperse again to obtain the fluorescent substance included silica nanoparticle bonded with the anti HER2 antibody.

The fluorescent substance included silica nanoparticle bonded with the anti HER2 antibody obtained with the nanoparticle 1 as the starting material is to be the indicator material A, and the fluorescent substance included silica nanoparticle bonded with the anti HER2 antibody obtained with the nanoparticle 2 as the starting material is to be the indicator material B.

As the comparison example, the anti HER2 antibody is bonded to the Cy5 to obtain reduced anti HER antibody solution (indicator material D). Similarly, the indicator material C is made by bonding the anti HER2 antibody to the CdSe.

[Staining Tissue Using Fluorescent Substance Included Nanoparticle]

According to the method including the following steps (1) to (10), the made antibody bonded indicator materials A to D are used to perform immunostaining using adjacent slices of human breast tissue with which the FISH score is measured in advance. A tissue array slide (CB-A712) of Cosmobio is used as the stain slice. 24 slices with a FISH score from 1 to 9 are used.

step (1): The pathological slice is immersed in a container with xylene for 30 minutes. The xylene is changed 3 times during the process.

step (2): The pathological slice is immersed in a container with ethanol for 30 minutes. The ethanol is changed 3 times during the process.

step (3): The pathological slice is immersed in a container with water for 30 minutes. The water is changed 3 times during the process.

step (4): The pathological slice is immersed in 10 mM citric acid buffered solution (pH 6.0) for 30 minutes.

step (5): The autoclave processing is performed for 10 minutes at 121 degrees.

step (6): A slice after autoclave processing is immersed in a container with PBS for 30 minutes.

step (7): 1% BSA included PBS is placed on the tissue and left as is for 1 hour.

step (8): The indicator materials A to D bonded with anti HER2 antibody which are diluted by the 1% BSA included PBS to 0.05 nM are placed on each tissue slice and left as is for 3 hours.

step (9): Each slice after staining is immersed in a container with PBS for 30 minutes.

step (10): After dropping Aquatex by Merck Chemical, the cover glass is placed to be sealed.

[Experiment Results]

A plurality of fluorescent images are obtained changing the field (observation area) of the tissue slice stained using each indicator material A to D, and the number of fluorescent bright points (bright point number) is measured from each fluorescent image with the image analysis software.

An upright microscope Axio Imager M2 manufactured by Carl Zeiss is used as the microscope. An objective lens is set to 20 times, an excitation light with a wavelength of 630 to 670 nm is irradiated, fluorescence emitted from a tissue slice is imaged, a fluorescent image (image data) is obtained with the camera attached to the microscope (monochrome), and the bright point number is measured with the image analysis software. Regarding the camera, the pixel size is 6.4 μm×6.4 μm, the vertical number of pixels is 1040 pixels, and the horizontal number of pixels is 1388 pixels (imaging region 8.9 mm×6.7 mm).

Regarding each indicator material A to D, the correlation coefficient R between the measured bright point number and the FISH score is calculated for each field. The FISH score corresponds to the overexpression level of the HER2 gene, and the higher the value of the FISH score is, this shows that the overexpression level of the HER 2 gene is high.

Figure 5:
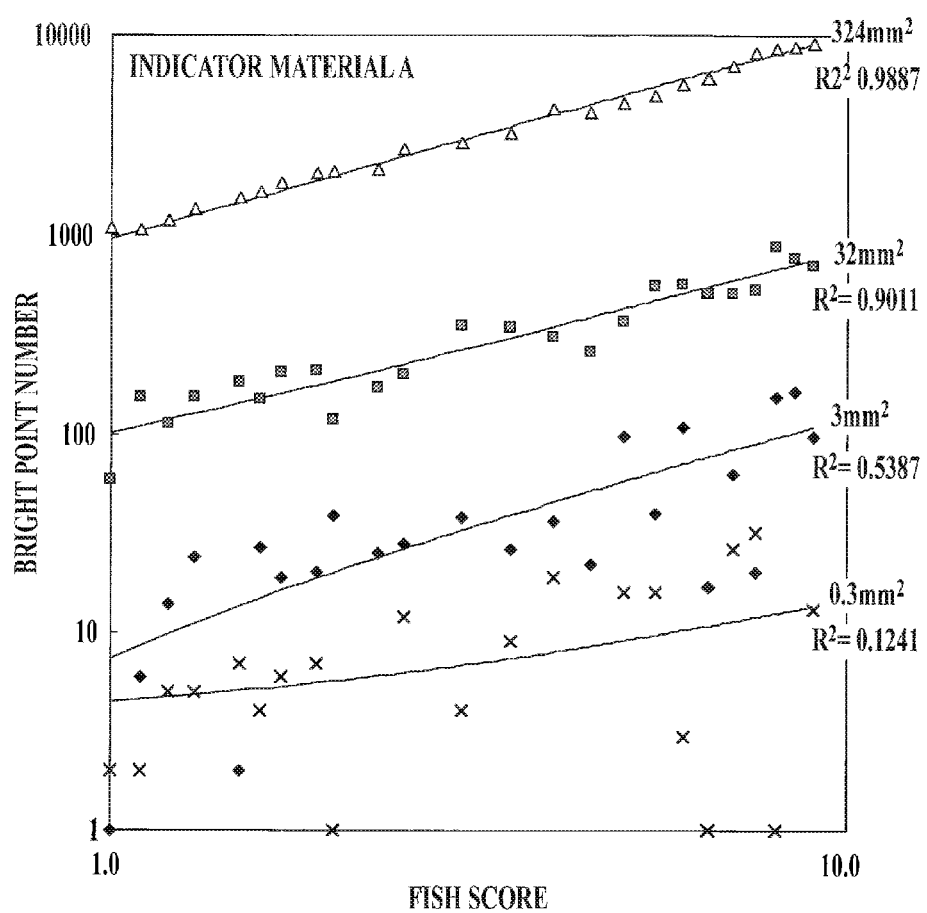
FIG. 5 is a diagram showing a relation between a bright point number and a FISH score when an indicator material A is used.

FIG. 5 is a diagram showing a relation between the bright point number measured from the fluorescent images with a plurality of different fields (0.3 $mm^2$, 3 $mm^2$, 32 $mm^2$, 324 $mm^2$) and the FISH score when the indicator material A (Cy5 included indicator material) is used. The value of $R^2$ shown in the diagram is a square value of the correlation coefficient between the bright point number and the FISH score.

Figure 6:
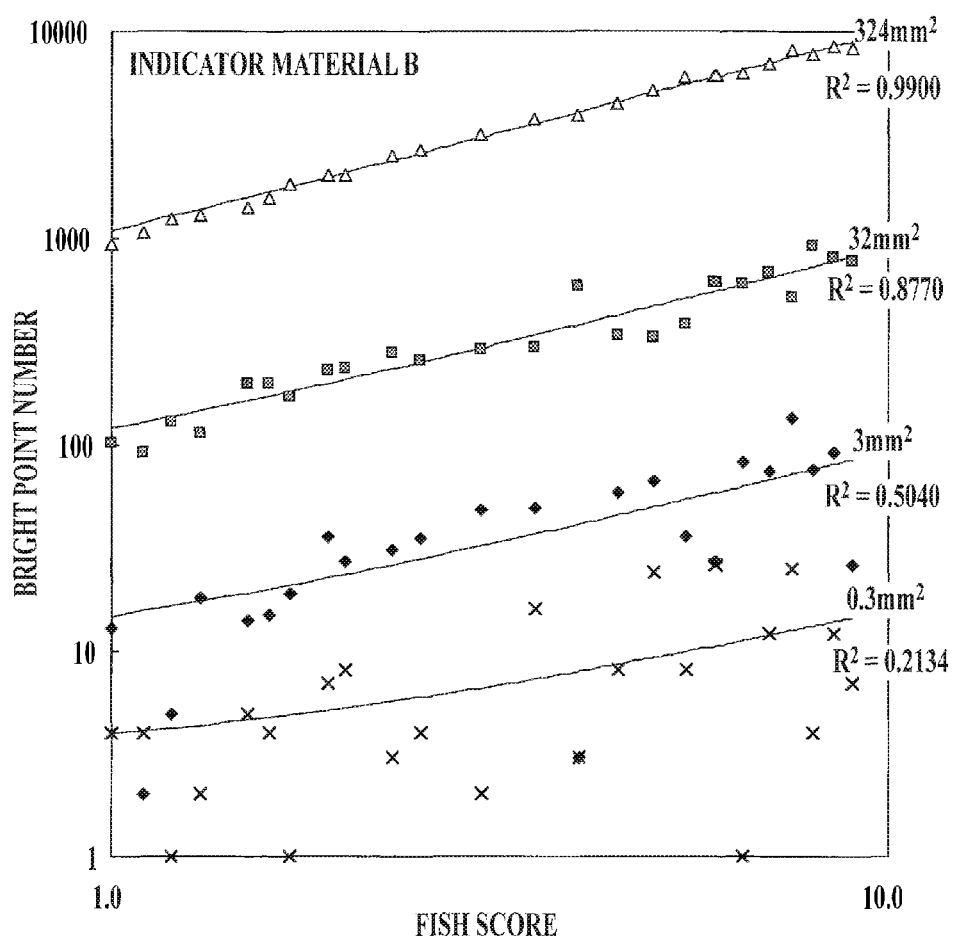
FIG. 6 is a diagram showing a relation between a bright point number and a FISH score when an indicator material B is used.

FIG. 6 is a diagram showing a relation between the bright point number measured from the fluorescent images with a plurality of different fields (0.3 mm², 3 mm², 32 mm², 324 mm²) and the FISH score when the indicator material B (CdSe included indicator material) is used.

Figure 7:
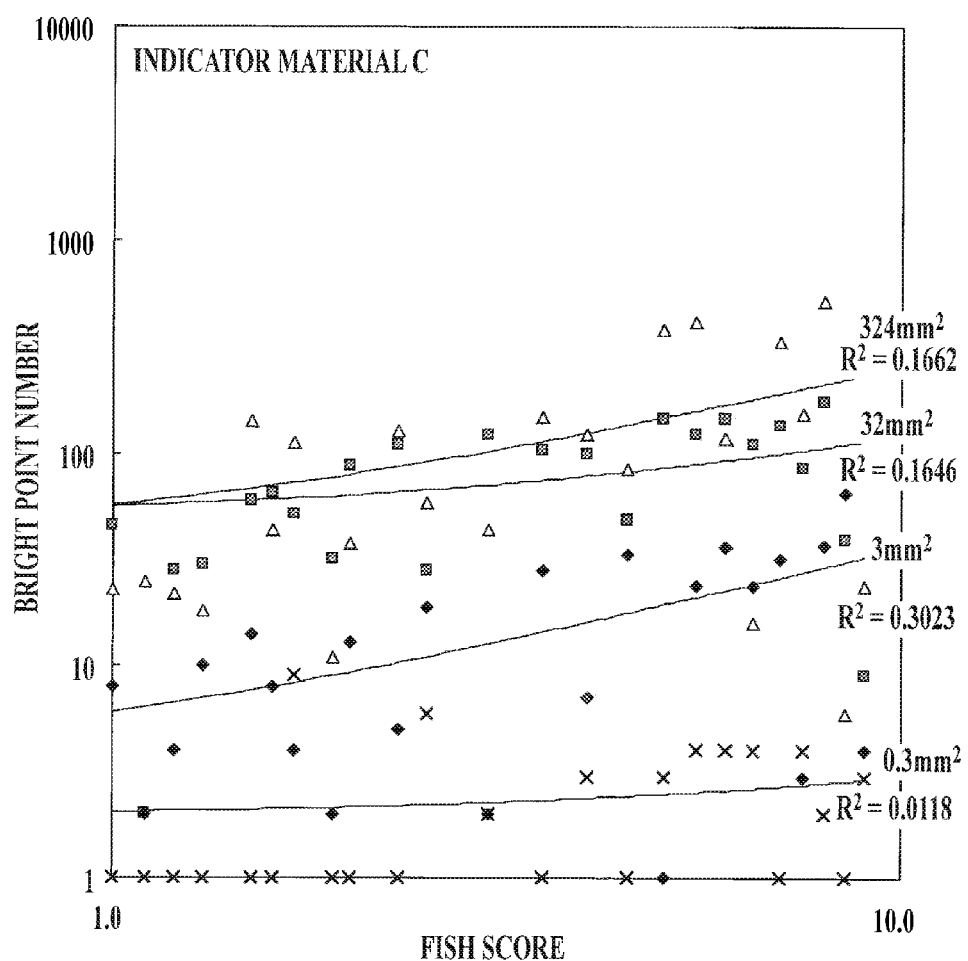
FIG. 7 is a diagram showing a relation between a bright point number and a FISH score when an indicator material C is used.

FIG. 7 is a diagram showing a relation between the bright point number measured from the fluorescent images with a plurality of different fields (0.3 mm², 3 mm², 32 mm², 324 mm²) and the FISH score when the indicator material C (CdSe) is used.

Figure 8:
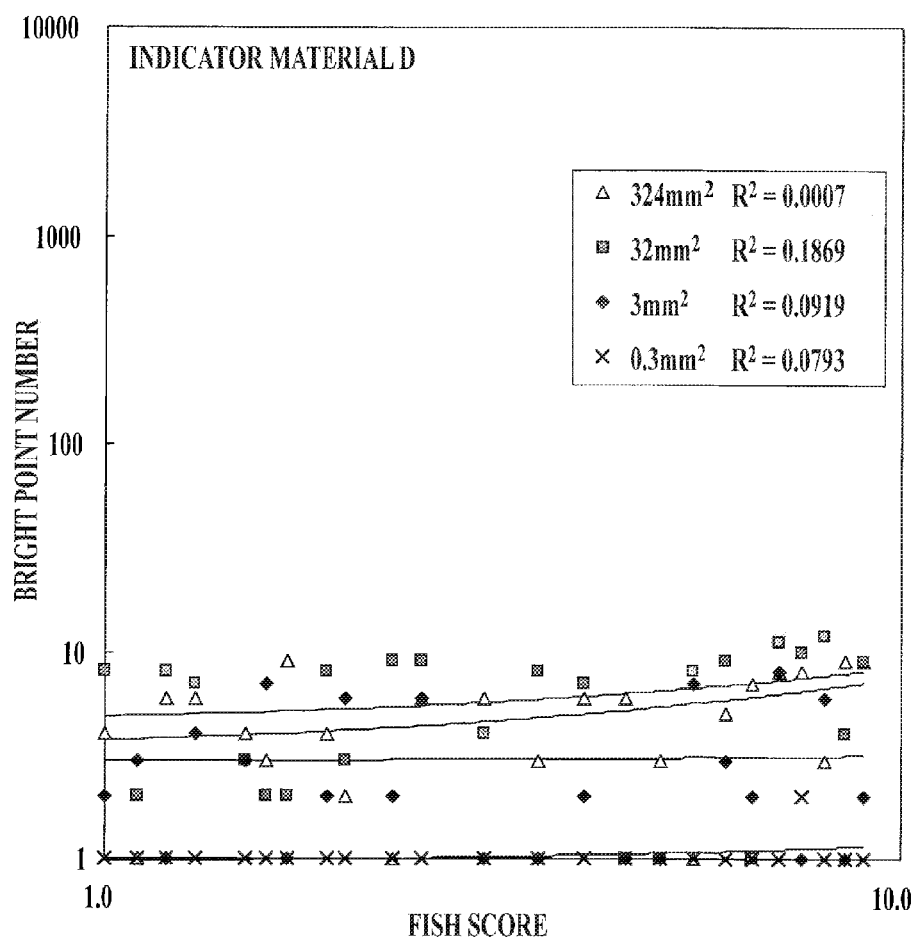
FIG. 8 is a diagram showing a relation between a bright point number and a FISH score when an indicator material D is used.

FIG. 8 is a diagram showing a relation between the bright point number measured from the fluorescent images with a plurality of different fields (0.3 mm², 3 mm², 32 mm², 324 mm²) and the FISH score when the indicator material D (Cy5) is used.

Figure 9:
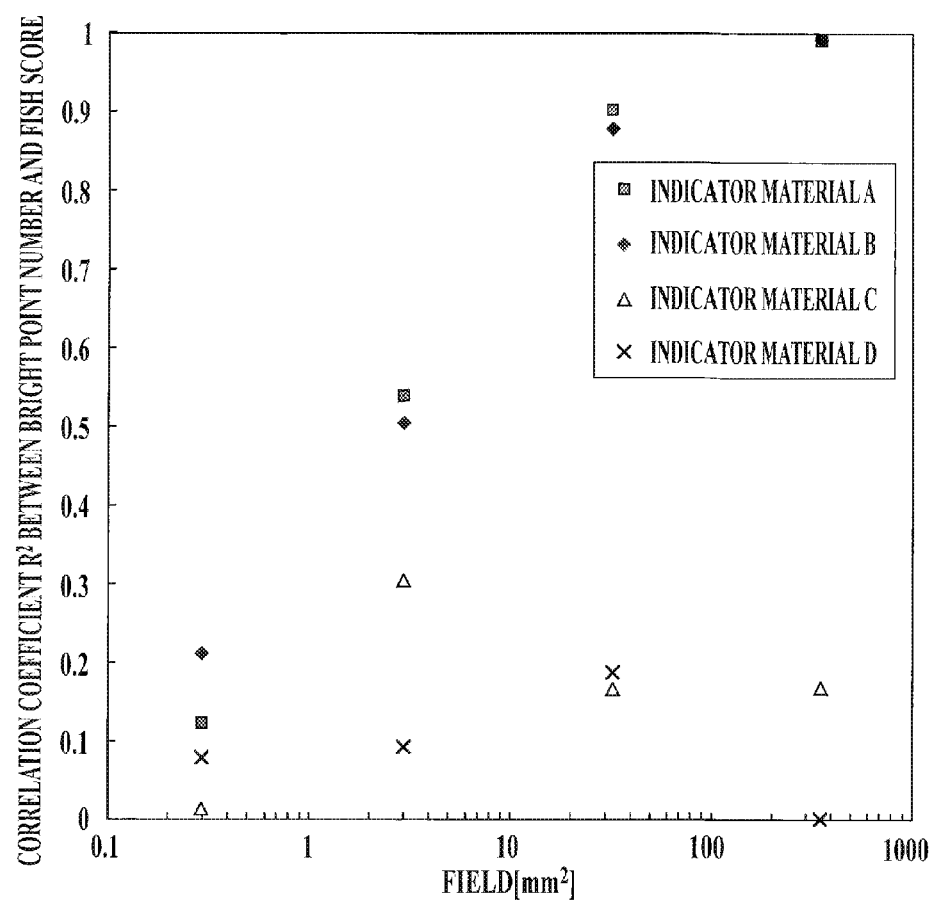
FIG. 9 is a diagram showing a square value of a correlation coefficient between a bright point number and a FISH score measured from a microscopic image of each field in each indicator material A to D.

Table 1 and FIG. 9 show a square value ($R^2$) of the correlation coefficient between the bright point number measured from the fluorescent image of each field (observation area) and the FISH score for each indicator material A to D.

TABLE 1

| INDICATOR MATERIAL | FIELD (OBSERVATION AREA) | CORRELATION COEFFICIENT $R^2$ BETWEEN BRIGHT POINT NUMBER AND FISH SCORE |
|---|---|---|
| INDICATOR MATERIAL A | 0.3 mm² | 0.1241 |
|  | 3 mm² | 0.5387 |
|  | 32 mm² | 0.9011 |
|  | 324 mm² | 0.9887 |
| INDICATOR MATERIAL B | 0.3 mm² | 0.2134 |
|  | 3 mm² | 0.5040 |
|  | 32 mm² | 0.8770 |
|  | 324 mm² | 0.9900 |
| INDICATOR MATERIAL C | 0.3 mm² | 0.0118 |
|  | 3 mm² | 0 3023 |
|  | 32 mm² | 0.1646 |
|  | 324 mm² | 0.1662 |
| INDICATOR MATERIAL D | 0.3 mm² | 0.0793 |
|  | 3 mm² | 0.0919 |
|  | 32 mm² | 0.1869 |
|  | 324 mm² | 0.0007 |

When the indicator material A is used to stain the tissue slice and the bright point number is measured from the fluorescent image with a field of 0.3 mm², the square value ($R^2$) of the correlation coefficient between the bright point number and the FISH score is 0.1241 and no correlation can be seen between the bright point number and the FISH score. It is assumed this is because the field of 0.3 mm² is too small and the variation is large.

When the indicator material A is used to stain the tissue slice and the bright point number is measured from the fluorescent image with a field of 3 mm², the square value ($R^2$) of the correlation coefficient between the bright point number and the FISH score is 0.5387. When converted to the correlation coefficient R, this value is about 0.734, and it can be said that there is a strong correlation between the bright point number and the FISH score.

When the indicator material A is used to stain the tissue slice and the bright point number is measured from the fluorescent image with a field of 32 mm², the square value ($R^2$) of the correlation coefficient between the bright point number and the FISH score is 0.9011. It can be said that the correlation is stronger when the field is 32 mm² compared to when the field is 3 mm².

When the indicator material A is used to stain the tissue slice and the bright point number is measured from the fluorescent image with a field of 324 mm², the square value ($R^2$) of the correlation coefficient between the bright point number and the FISH score is 0.9887. It can be said that the correlation is stronger when the field is 324 mm² compared to when the field is 32 mm².

Similarly, when the indicator material B is used, in a field equal to or larger than 3 mm², it is found that there is correlation between the bright point number and the FISH score, and the correlation coefficient becomes larger as the field becomes larger.

From the result of using the indicator materials A and B, it is found that the square value ($R^2$) of the correlation coefficient between the bright point number and the FISH score is close enough to 1 when the field is 324 mm².

On the other hand, when the tissue slice is stained using the indicator material C or indicator material D, correlation cannot be seen between the bright point number and the FISH score.

Moreover, even if the focus of the microscope is slightly moved to the upper portion or the lower portion in the thickness (normally, a few μm) of the observation target tissue slice, a significant difference in the situation cannot be seen.

From the above results, when the tissue slice using the indicator materials A and B is observed with a large field, it is found that the correlation between the bright point number and the FISH score is good, and the expression level of the $HER^2$ can be evaluated based on the bright point number. In other words, instead of using a troublesome method such as the FISH method, by staining the tissue slice with the stain reagent of the fluorescent substance included nanoparticle bonded with the biological substance recognition site which recognizes a specific biological substance, and measuring the bright point number from the image with the field of 3 mm² or larger obtained by imaging the above enlarged with the microscope and capturing the image, the expression level of the specific biological substance can be evaluated. The above is effective as a method to replace the FISH method.

The indicator materials A and B use particles including a fluorescent substance, and has a larger brightness compared to the indicator materials C and D which use the fluorescent substance as a simple substance. Therefore, each one of the bright points can be identified easily from the image, and the bright point number can be calculated accurately.

<Operation of Pathological Diagnosis Assistance System 100>

Below, the operation of obtaining the above described fluorescent image and the bright field image and performing analysis in the pathological diagnosis assistance system 100 is described. In the description below, the observation target is the tissue slice stained using the stain reagent including the fluorescent substance included nanoparticle bonded with the biological substance recognition site which recognizes a specific protein (For example, HER 2 protein in breast cancer tissue. Hereinafter referred to as specific protein). However, the observation target is not limited to the above.

First, the bright field image and the fluorescent image are obtained with the microscopic image obtaining apparatus 1A by steps (a1) to (a5).

(a1) The operator places a slide on which the tissue slice stained with the stain reagent including the fluorescent substance included nanoparticle bonded with the biological substance recognition site which recognizes the specific protein as the fluorescent indicator material and the HE agent on the slide fixing stage of the microscopic image obtaining apparatus 1A.

(a2) The bright field unit is set, the capturing magnification and focus are adjusted, and the region of the observation target on the tissue is positioned in the field.

(a3) Capturing is performed with the capturing unit to generate the image data of the bright field image, and the image data is transmitted to the image processor 2A.

(a4) The unit is changed to the fluorescent unit.

(a5) Capturing is performed with the capturing unit without changing the field and the capturing magnification to generate the image data of the fluorescent image, and the image data is transmitted to the image processor 2A.

As described above, in the microscopic image obtaining apparatus 1A, the bright field image and the fluorescent image are obtained from the slide with the same tissue slice with the same capturing magnification within the same range (same field). Therefore, the same coordinate position in the bright field image and the fluorescent image show the same position in the tissue slice, and positions do not need to be matched between the two images.

According to consideration by the inventors, etc. of the present application, when the HE staining and the staining by the fluorescent substance included nanoparticle are performed at the same time, if the fluorescent bright point of the fluorescent substance included nanoparticle has a luminescence amount difference of 10% (1.1 times) or more from the autofluorescence of the tissue and the light emission of the eosin (background), the automatic processing of detecting the fluorescent bright point from the microscopic image is possible under any of the processing systems of 8 bits (0 to 255 tones) and 12 bits (0 to 4095 tones). When only the staining by the fluorescent substance included nanoparticle is performed, if the fluorescent substance included nanoparticle has a luminescence amount difference of 10% (1.1 times) or more from the autofluorescence of the tissue, the automatic processing of detecting the fluorescent bright point is possible under any of the processing systems of 8 bits (0 to 255 tones) and 12 bits (0 to 4095 tones). Therefore, preferably, the excitation light wavelength in the fluorescent unit is selected from within the range of 560 to 630 nm, and the fluorescent substance used emits fluorescence including a peak within the range of 580 to 690 nm, more preferably within the range of 600 to 630 nm by the excitation light. If the fluorescent substance includes a peak within the above range, when the excitation light within the above range is selected, it is possible to secure the luminescence difference between the autofluorescence of the tissue including light emission of eosin and fluorescence from the fluorescent substance included nanoparticle, and with this, it is possible to surely distinguish and recognize the difference between the above (luminescence difference of the above being 10% (1.1 times) or more).

When the HE staining is not performed at the same time, the autofluorescence of the tissue is very weak, and therefore, even if the range of the wavelength of the excitation light is not limited within the typical range of 200 nm to 700 nm, it is possible to secure the luminescence difference between the autofluorescence and fluorescence from the fluorescent substance included nanoparticle, and with this, it is possible to surely distinguish and recognize the difference between the above (luminescence difference of the above being 10% (1.1 times) or more).

In the image processor 2A, image analysis processing A is performed based on the bright field image and the fluorescent image.

Figure 10:
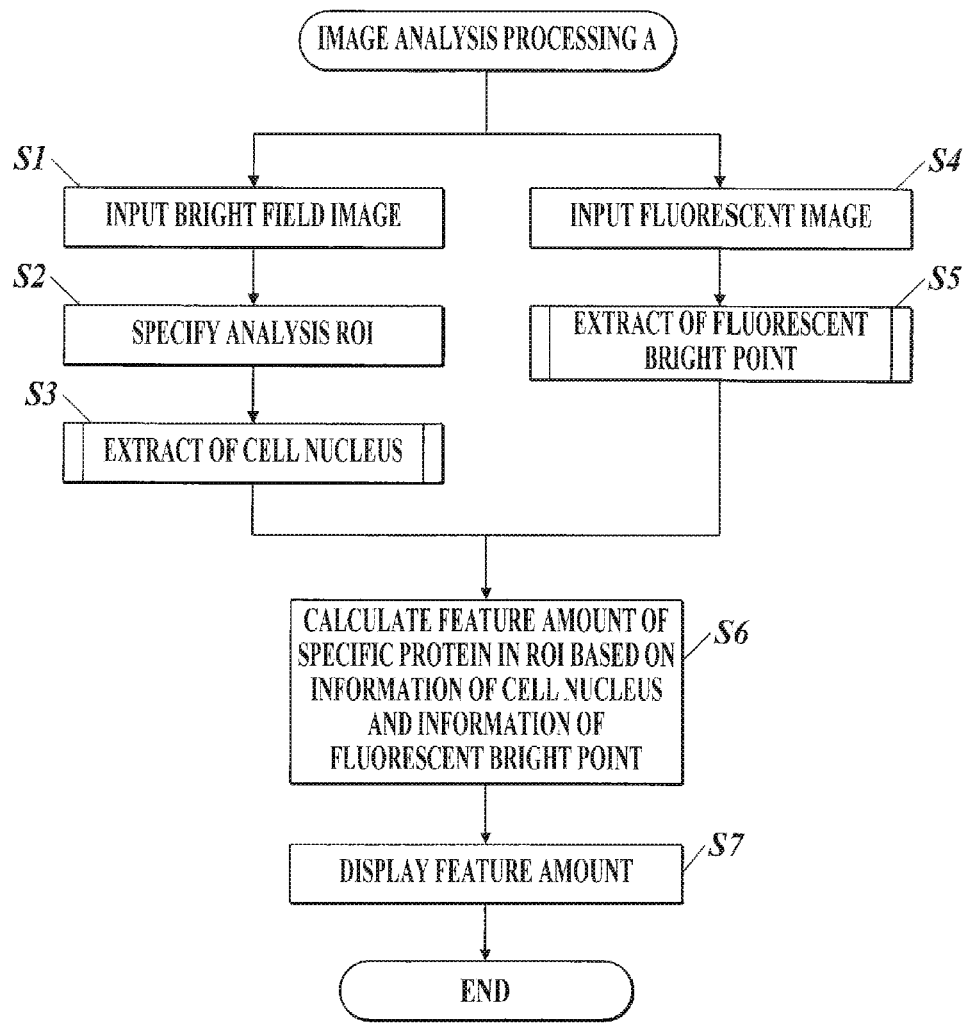
FIG. 10 is a flowchart showing image analysis processing A performed by a control section of FIG. 2 in the first embodiment.

FIG. 10 shows a flowchart of the image analysis processing A in the image processor 2A. The image analysis processing shown in FIG. 10 is performed by the control section 21 in coordination with the program stored in the storage section 25.

When the bright field image is input from the microscopic image obtaining apparatus 1A through the communication I/F 24 (step S1), the ROI of the analysis target is specified from the bright field image (step S2).

In step S2, first, when the bright field image capturing the tissue slice is displayed on the display section 23, and a region is specified with the operation section 22 from the displayed bright field image, the specified region is set as the ROI (region of interest) which is the analysis target.

Figure 11:
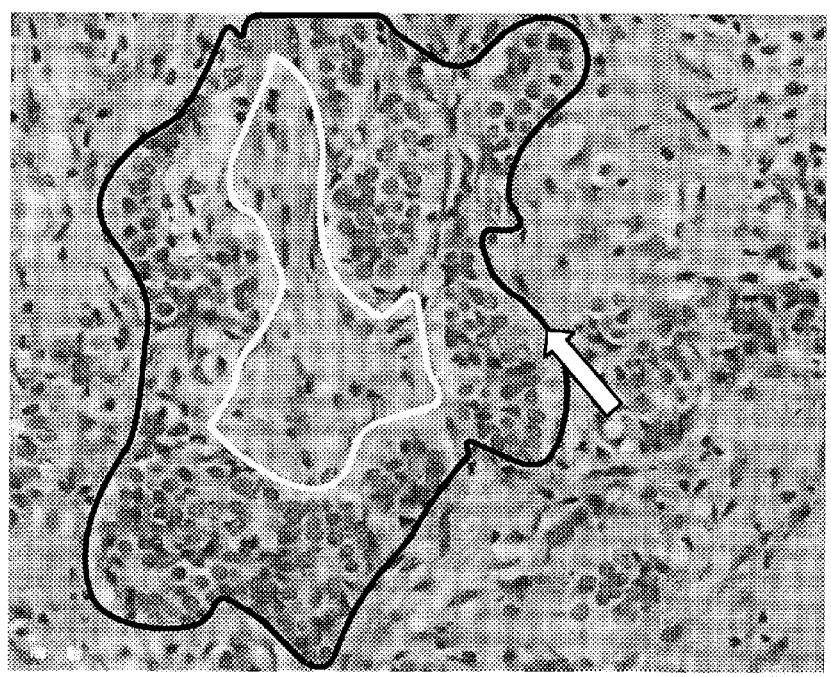
FIG. 11 is a diagram describing specification of ROI.

FIG. 11 shows an example of specifying the ROI in step S2. Here, the bright field image, especially the HE stained image is the image conventionally used by the physician in pathological diagnosis. For example, as shown in FIG. 11, the region determined as the region with a doubt of cancer such as a region where many cell nuclei are gathered, a region where size of the cell nuclei are varied, a region where the cell nuclei is larger than normal, etc. in the bright field image can be specified as the ROI of the analysis target.

As the ROI, the entire image can be specified or an arbitrary region can be specified. The region where the physician as the user would like to know the expression amount of the specific protein quantitatively can be specified as the arbitrary region, for example, a cancer region, invasion portion where the cancer is enlarged to the surroundings, and the like. The arbitrary region can be specified by specifying a geometric region such as a rectangle, a circle, etc., or the user can draw curves freely with a mouse, etc.

Next, the region of the cell nucleus is extracted from the bright field image (step S3).

Figure 12:
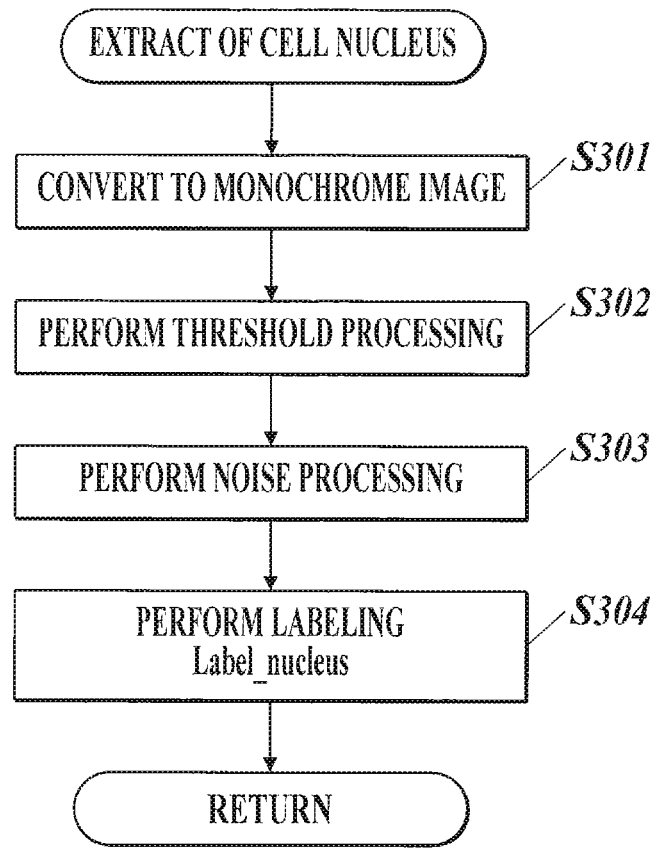
FIG. 12 is a flowchart showing details of processing of step S3 in FIG. 10.

FIG. 12 shows a detailed flow of the processing in step S3. The processing in step S3 is performed by the control section 21 in coordination with the program stored in the storage section 25.

In step S3, first, the conversion of the bright field image to the monochrome image is performed (step S301).

Figure 13:
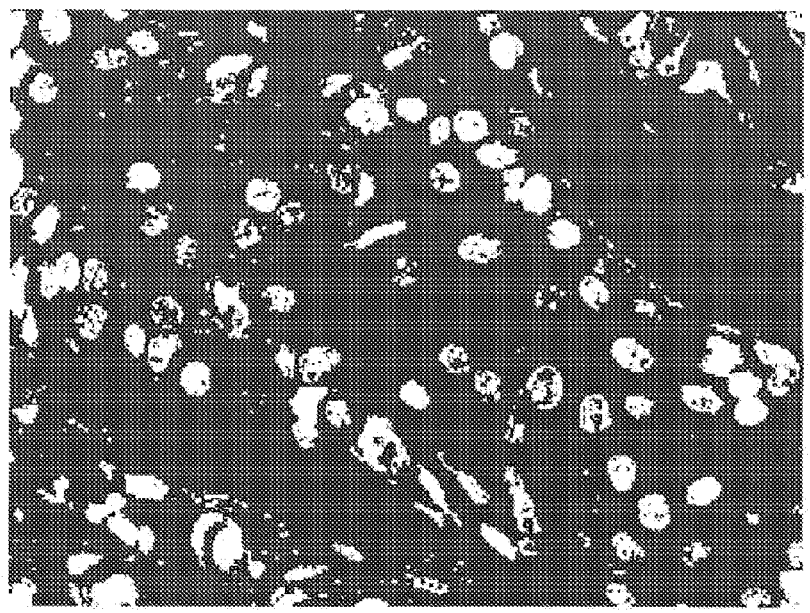
FIG. 13 is a diagram showing an example of a binary image after threshold processing.

Then, threshold processing is performed on the monochrome image using a threshold determined in advance, and each pixel is binarized (step S302). FIG. 13 shows an example of a binary image after threshold processing.

Figure 14:
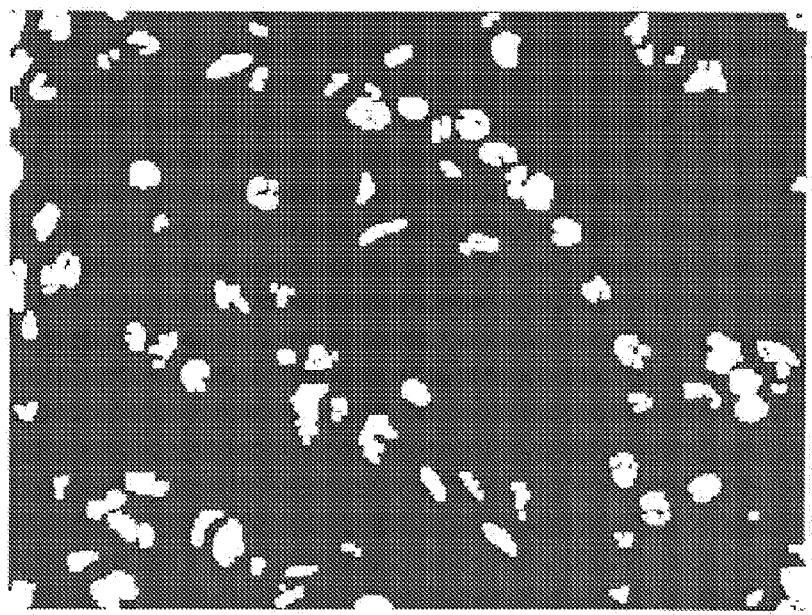
FIG. 14 is a diagram showing an example of a binary image after removing noise.

Next, noise removal is performed (step S303). Specifically, the noise removal can be performed by performing closing processing on the binary image. The closing processing is processing of performing dilation processing and then erosion processing the same number of times. The dilation processing is processing of replacing the target pixel with a white pixel when any of the pixels within the range of n×n pixels (n is an integer of 2 or more) from the target pixel is white. The erosion processing is processing of replacing the target pixel with a black pixel when any of the pixels within the range of n×n pixels from the target pixel is black. Small regions such as noise can be removed with the closing processing. FIG. 14 shows an example of an image after noise removal. As shown in FIG. 14, after the noise removal, an image (cell nucleus image) with the cell nucleus extracted can be obtained.

Next, labeling processing is performed on the image after noise removal, and a label Label_nucleus is attached to each extracted cell nucleus (step S304). The labeling processing is processing of attaching the same label (number) to the connecting pixels to identify the object in the image. According to the labeling processing, each cell nucleus can be identified from the image after noise removal and a label can be attached.

In order to distinguish the above from the label number in extracting the fluorescent bright point as described later, when the maximum value which the computer can hold is MAX, and the number of times of labeling up to the present point is Label_temp, MAX-Label_temp is attached to the new cell nucleus as the label Label_nucleus. For example, when a label is attached to the 101-st cell nucleus, since Label_temp=100, if MAX=65536, 65436 is attached as the Label_nucleus. After labeling processing the processing advances to step S6 of FIG. 10.

Figure 15:
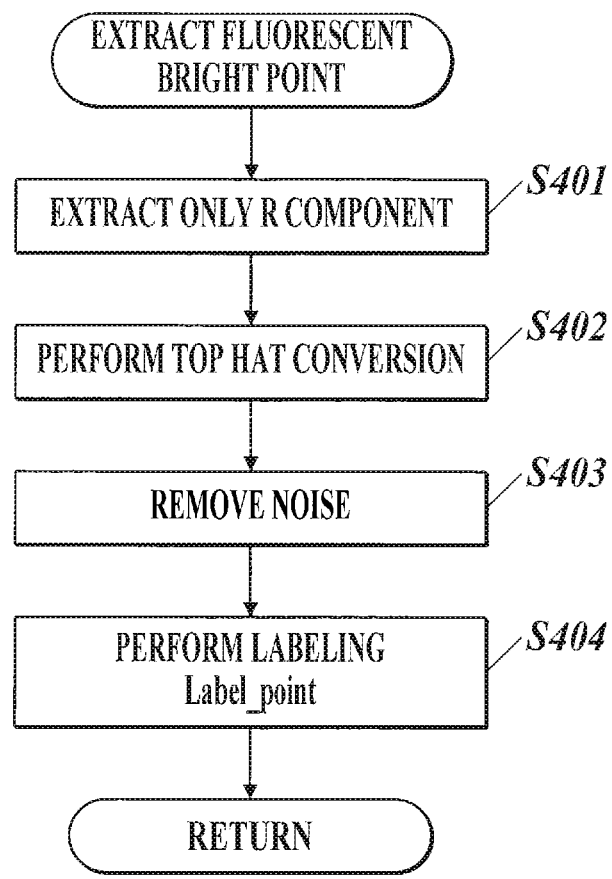
FIG. 15 is a flowchart showing details of processing of step S5 of FIG. 10.

In step S4 of FIG. 10, when a fluorescent image is input from a microscopic image obtaining apparatus 1A through a communication I/F 24 (step S4), the fluorescent bright point is extracted from the fluorescent image (step S5). FIG. 15 shows a detailed flow of processing in step S5. The processing of step S5 is performed by the control section 21 in coordination with a program stored in the storage section 25.

First, an R component is extracted from the fluorescent image (step S401).

Figure 16:
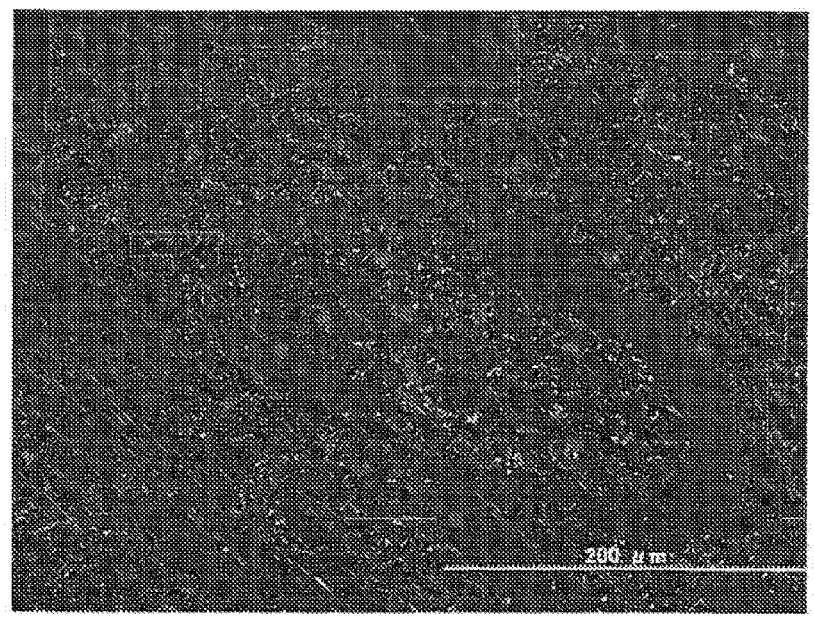
FIG. 16 is a diagram showing an example of a fluorescent bright point candidate image.

Next, Top hat conversion is performed on an image from which the R component is extracted (step S402). Top hat conversion is processing where a value of a pixel corresponding to the image of multiplying the minimum value filter and the maximum value filter to the input image in this order is subtracted from the value of each pixel of the input image. The minimum value filter replaces the value of the target pixel with the minimum value among the neighboring pixels (for example, 3×3 pixels) of the target pixel. The maximum value filter replaces the value of the target pixel with the maximum value among the neighboring pixels (for example, 3×3 pixels) of the target pixel. According to Top hat conversion, a small projection (region where brightness is high compared to neighboring pixels) on a gradation profile can be extracted. With this, the fluorescent bright point candidate image can be obtained. FIG. 16 shows an example of a fluorescent bright point candidate image.

Figure 17:
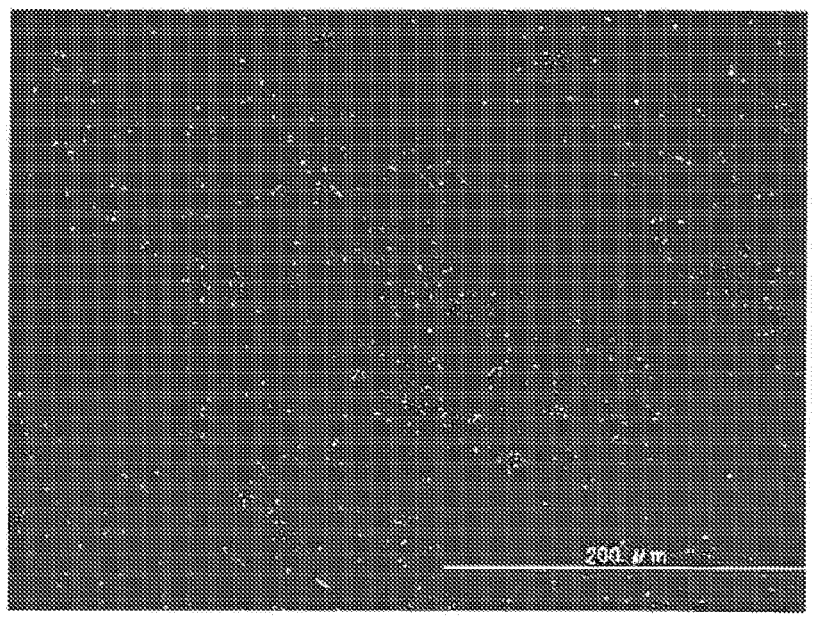
FIG. 17 is a diagram showing an example of a fluorescent bright point image obtained after noise removal in the fluorescent bright point candidate image shown in FIG. 16.

Next, noise is removed from the fluorescent bright point candidate image, and the image (fluorescent bright point image) with the fluorescent bright point extracted is obtained (step S403). FIG. 17 shows the fluorescent bright point image with the fluorescent bright point extracted obtained after noise removal from the fluorescent bright point candidate image shown in FIG. 16.

Then, after labeling processing is performed on the image after noise removal, the label Label_point is attached to each of the extracted fluorescent bright point (step S404). Label_point is attached in order from 1. After the labeling processing ends, the processing advances to step S6 of FIG. 10.

In step S6 of FIG. 10, the feature amount showing the expression amount of the specific protein in the ROI is calculated based on the region of the extracted cell nucleus and the fluorescent bright point (step S6).

Figure 18:
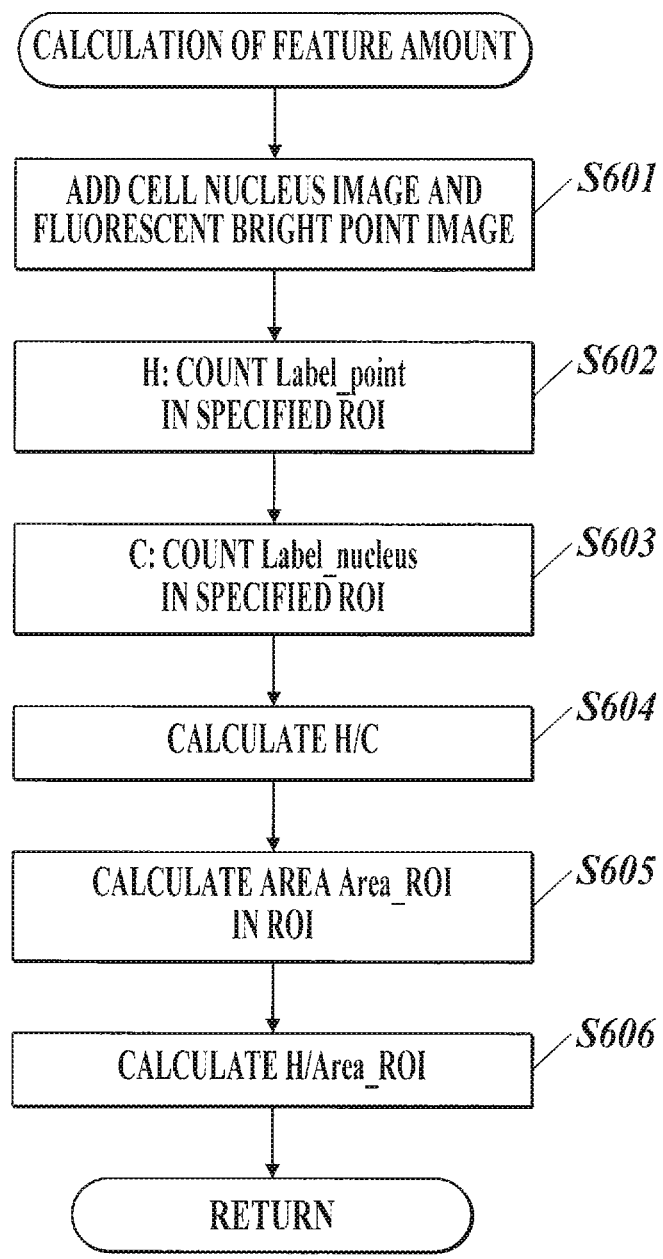
FIG. 18 is a flowchart showing details of processing of step S6 of FIG. 10.

FIG. 18 shows a detailed flow of the processing in step S6. The processing of step S6 is performed by the control section 21 in coordination with the program stored in the storage section 25.

First, the value of each pixel of the cell nucleus image and the value of the corresponding pixel in the fluorescent bright point image are added to create a synthetic image (step S601). Next, number H of the Label_point attached in the ROI specified in step S2 is counted (step S602). Next, number C of the Label_nucleus attached in the ROI specified in step S2 is counted (step S603), and H/C is calculated (step S604). H/C is a fluorescent bright point number for each cell nucleus in the ROI.

When the area in the ROI Area_ROI is calculated (step S605), and H/Area_ROI is calculated (step S606), The processing advances to step S7 of FIG. 10. The area Area_ROI is calculated based on the pixel number in the ROI.

In step S7 of FIG. 10, the calculated feature amount is output as display on the display section 23 (step S7).

Figure 19:
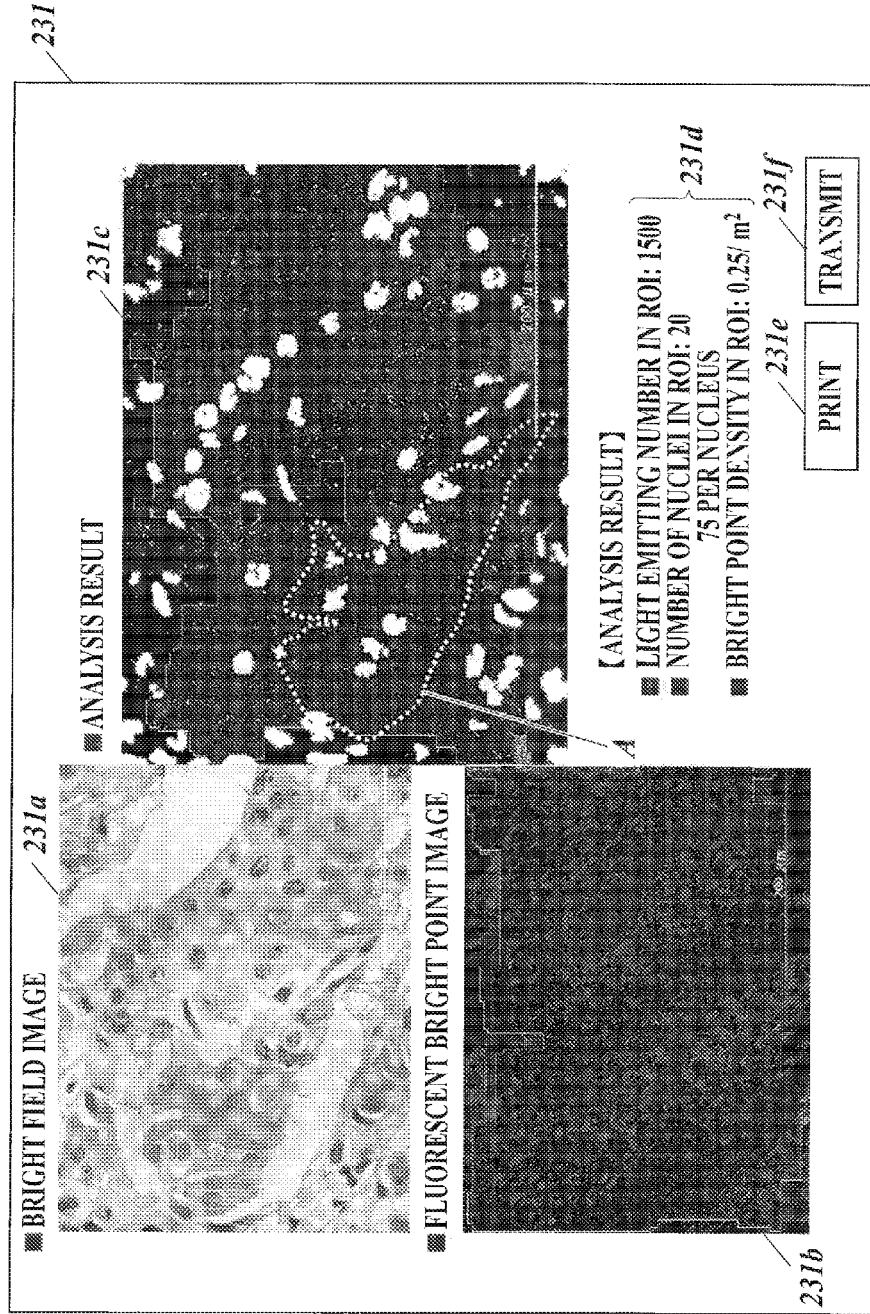
FIG. 19 is a diagram showing an example of an analysis result screen.

FIG. 19 is a diagram showing an example of an analysis result screen 231 displayed on the display section 23 in step S7. As shown in FIG. 19, the following are displayed in the analysis result screen 231, a bright field image 231a used in calculating the feature amount, a fluorescent image 231b, a synthesis image 231c made by adding the cell nucleus image and the fluorescent bright point image extracted from the above images, a feature amount 231d obtained by analysis, a print button 231e, and a transmit button 231f. As shown in FIG. 19, an annotation (a frame border) A showing the region of the ROI specified in step S2 is displayed overlapped in the synthesis image 231c.

As the feature amount 231d, the following are displayed, the number of fluorescent bright points in the ROI (number H of Label_Point), the number of cell nuclei in the ROI (number C of Label_nucleus), the fluorescent bright number for each cell nucleus in the ROI (H/C), and the fluorescent bright point density in the ROI (H/Area_ROI). The fluorescent bright point shows the expression of the specific protein corresponding to the biological substance recognition site used in the staining reagent of the tissue slice. Therefore, by referring to the feature amount 231d of the above, the physician is able to understand the expression amount of the specific protein in the ROI quantitatively.

The HER2 protein is said to exist in the periphery of the cell membrane and is said to be related to the proliferation and malignant alteration of the cell through the signaling pathway. When there is cancer, overexpression of HER2 protein can be seen in the periphery of the cell membrane. In other words, overexpression of the HER2 protein can be seen in the cell membrane of the cancer cell. Therefore, the number of fluorescent bright points showing the expression of the HER2 protein in the ROI, specifically, the number of fluorescent bright points for each cell nucleus shows the amount of HER2 protein expressed in the periphery of the cell membrane for each cell in the ROI, and can be said to be a feature amount which quantitatively shows the degree of malignity of the cancer of the cell in the ROI. The fluorescent bright point density in the ROI shows expression amount of the HER2 protein which does not depend on the largeness of the region specified as the ROI, and can be said to be a feature amount which quantitatively shows the degree of malignity of the cancer in the ROI. Therefore, since the feature amount of the above is displayed, quantitative information for prognostic expectation and determining the future treatment plan can be provided to the physician.

Moreover, together with the feature amount 231d, the ROI and the synthesis image adding the cell nucleus image and the fluorescent bright point image are displayed in the analysis result screen 231. Therefore, the physician is able to confirm the size and the distribution of the cell nucleus in the ROI and confirm the expression of the specific protein in the image. Further, by also displaying the bright field image conventionally used in diagnosis by the physician and the fluorescent image extracting only the fluorescent bright point of the specific protein, it is possible to assist understanding the state of the cell in the ROI and the expression status of the specific protein.

For the ease of observation, any one or all of the bright field image 231a, the fluorescent image 231b, and the synthesis image 231C displayed on the analysis result screen 231 can be displayed enlarged or reduced.

The analysis result can be printed by pressing the print button 231e or output to external devices by pressing the transmit button 231f.

When the print button 231e is pressed on the operation section 22, the control section 21 transmits the data of the analysis result to a printer which is not shown through the communication I/F 24 or a communication network such as a LAN, etc., and the analysis result is printed. Alternatively, when the transmit button 231f is pressed on the operation section 22, the control section 21 transmits the data of the analysis result to the external device (for example, PACS (Picture Archiving and Communication System for medical application)) through the communication I/F 24 or the communication network such as a LAN, etc.

The analysis result which is output can be only the feature amount or can include any or all of the bright field image, the fluorescent image, and the synthesis image as in the display of the analysis result screen 231.

—Second Embodiment—

Next, the second embodiment of the present invention is described.

In the first embodiment, the analysis processing is performed using a bright field image and a fluorescent image. In the second embodiment described below, the analysis processing is performed by using only the fluorescent image of the tissue slice on which HE staining and staining with a staining reagent including a fluorescent substance included nanoparticle bonded with a biological substance recognition site which recognizes a specific protein.

The configuration of the pathological diagnosis assistance system 100 of the second embodiment is similar to the configuration described in the first embodiment. Therefore, the description is to be referred and the different portions are described below.

The fluorescent image is obtained with the microscopic image obtaining apparatus 1A by the following steps (b1) to (b3).

step (b1) The operator places a slide on which the tissue slice stained with the stain reagent including the fluorescent substance included nanoparticle bonded with the biological substance recognition site which recognizes the specific protein as the fluorescent indicator material and the HE reagent is placed on the slide fixing stage of the microscopic image obtaining apparatus 1A.

step (b2) The fluorescent unit is set, the capturing magnification and focus are adjusted, and the region of the observation target on the tissue is positioned in the field.

step (b3) Capturing is performed with the capturing unit to generate the image data of the fluorescent image, and the image data is transmitted to the image processor 2A.

In a case where the tissue slice is stained by HE staining together with staining by the predetermined fluorescent indicator material as described above, when the excitation light is irradiated with the fluorescent unit, the specific protein appears as the fluorescent bright point and the eosin which stains the cell cytoplasm emits light together with the autofluorescence of the tissue, etc. Here, the cell cytoplasm emits light due to the staining by the eosin, however, the cell nucleus does not emit light because it is not stained by the eosin, and the cell nucleus is shown blacker than the surrounding cell cytoplasm in the fluorescent image (see FIG. 21). Therefore, in the fluorescent image obtained by capturing with the fluorescent unit the tissue slice on which HE staining is performed together with the staining by the fluorescent indicator material, not only the fluorescent bright point but also the shape of the cell including the cell nucleus of the tissue slice is shown.

Then, in the image processor 2A, image analysis processing B is performed by extracting the region of the cell nucleus and the fluorescent bright point using only the fluorescent image obtained by the above steps (b1) to (b3) and calculating the feature amount showing the expression amount of the specific protein based on the above information.

Figure 20:
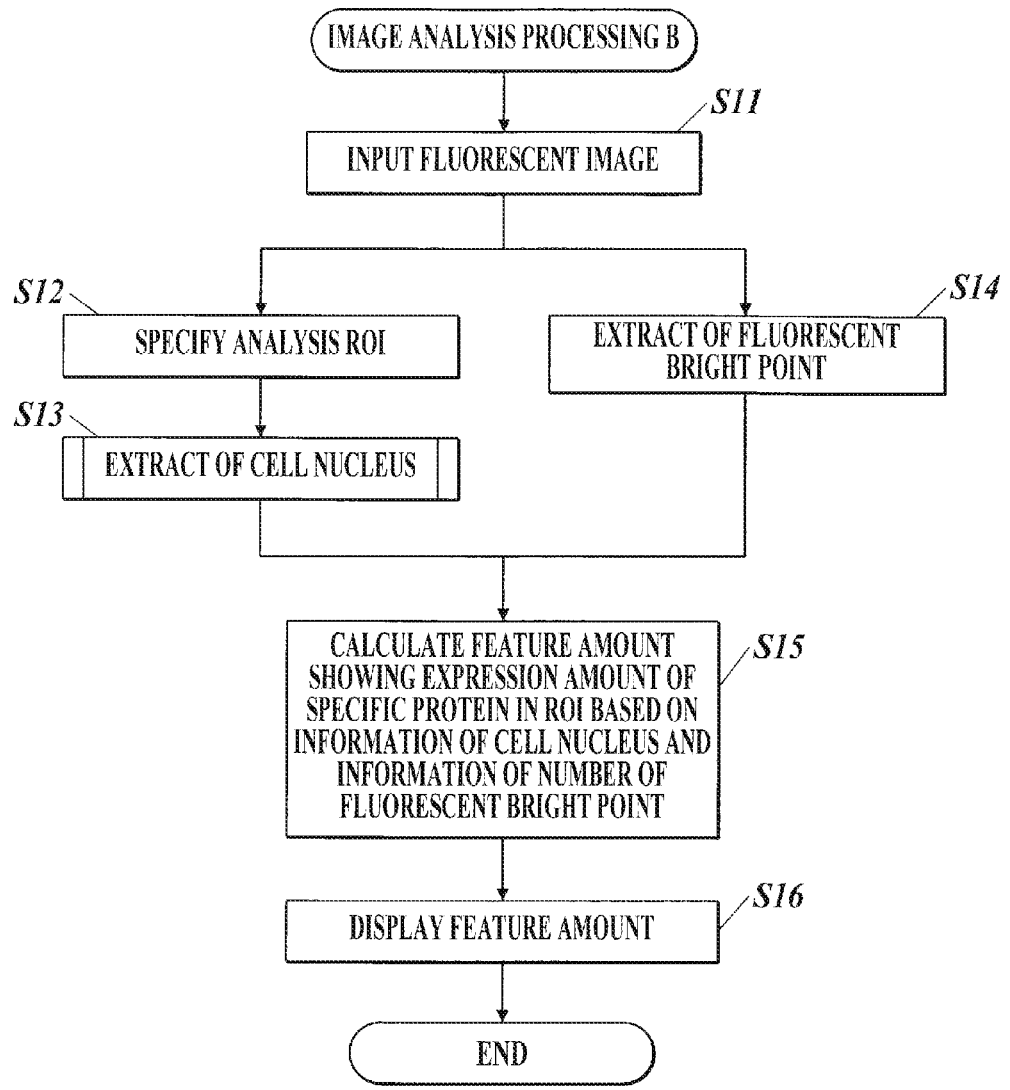
FIG. 20 is a flowchart showing image analysis processing B executed by a control section of FIG. 2 in the second embodiment.

FIG. 20 shows a flowchart of the image analysis processing B performed in the image processor 2A. The image analysis processing B shown in FIG. 20 is performed by the control section 21 in coordination with the program stored in the storage section 25.

When the fluorescent image is input from the microscopic image obtaining apparatus 1A (step S11), first, the processing of step S12 to step S13 to extract the cell nucleus and the processing of step S14 to extract the fluorescent bright point are performed.

In step S12, the ROI of the analysis target is specified from the fluorescent image (step S12).

Here, the minimum value filter processing is performed on the fluorescent image, and the fluorescent image after minimum value filter processing is displayed on the display section 23. When a region is specified on the operation section 22 from the displayed fluorescent image, the specified region is set as the ROI (region of interest).

Figure 21:
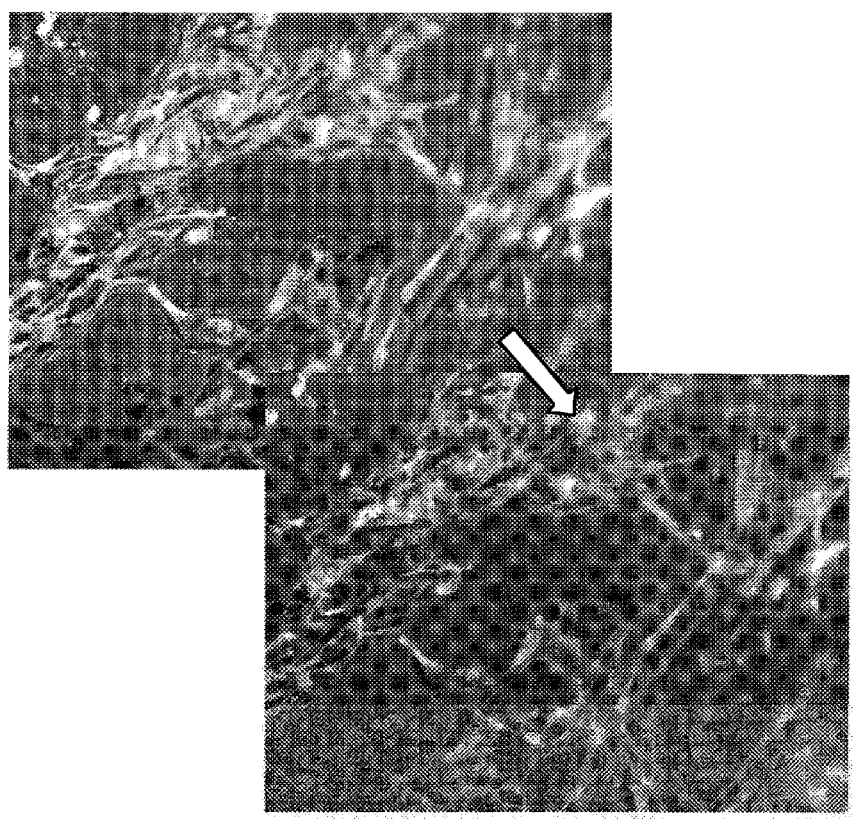
FIG. 21 is a diagram showing an example of a fluorescent image before and after minimum value filter processing.

FIG. 21 shows an example of a fluorescent image before and after minimum value filter processing. As shown in FIG. 21, by performing the minimum value filter processing, the fluorescent bright point can be removed from the fluorescent image. Therefore, the physician is able to easily observe the shape of the cell nucleus and the setting of the ROI becomes easy.

Next, the region of the cell nucleus is extracted from the fluorescent image (step S13).

Figure 22:
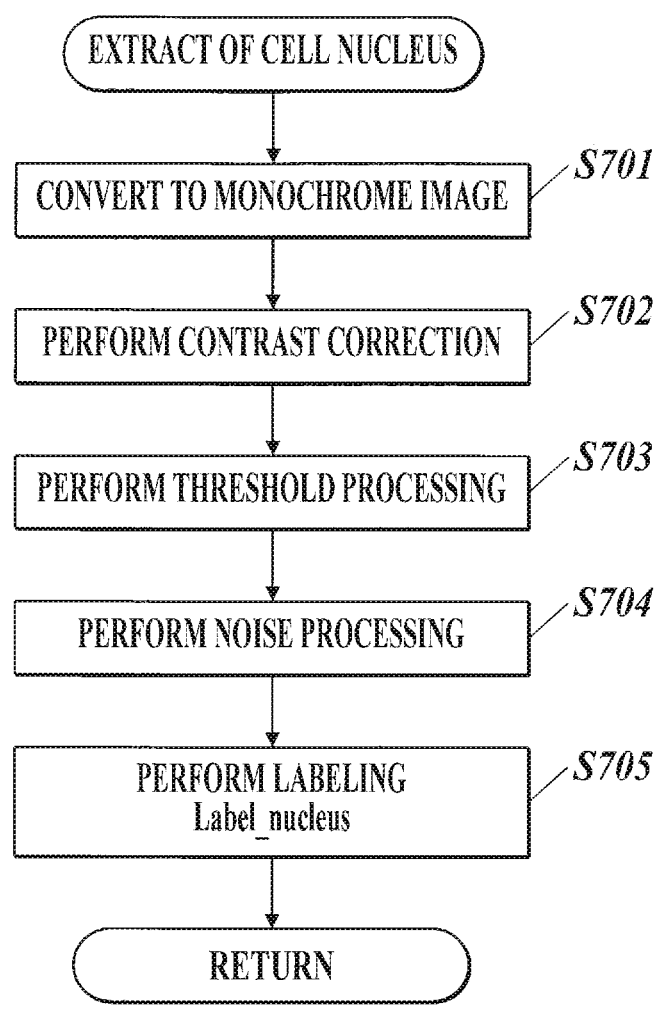
FIG. 22 is a flowchart showing details of processing of step S13 of FIG. 20.

FIG. 22 shows a detailed flow of the processing in step S13. The processing in step S13 is performed by the control section 21 in coordination with a program stored in the storage section 25.

In step S13, first, the conversion of the fluorescent image to the monochrome image is performed (step S701).

Next, contrast correction is performed on the monochrome image (step S702)

Figure 24A:
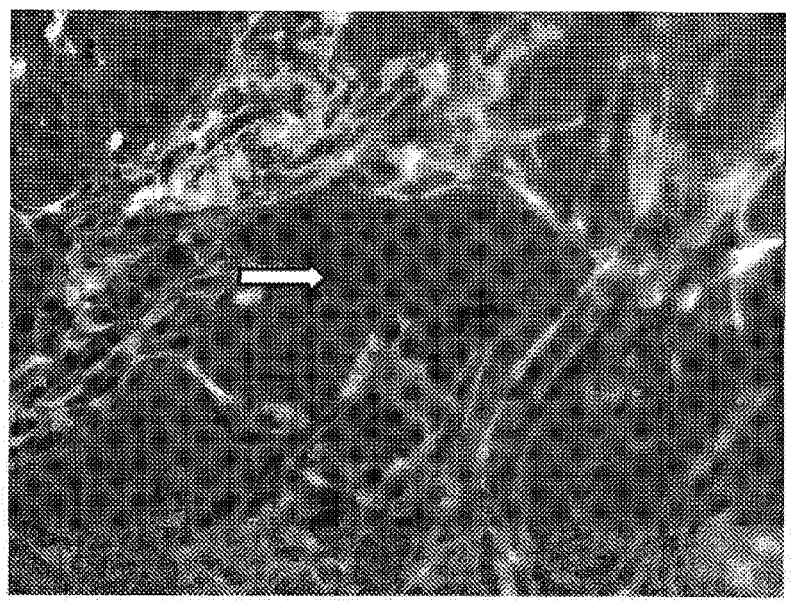
FIG. 24A is a diagram showing an example of a fluorescent image before gamma conversion.

In the fluorescent image, as shown in FIG. 24A, the contrast between the cell nucleus and the tissue surrounding the cell nucleus is small. In step S702, in order to emphasize the contrast in especially the high density region, processing is performed to enhance the contrast in the high density region by gamma conversion.

Figure 23:
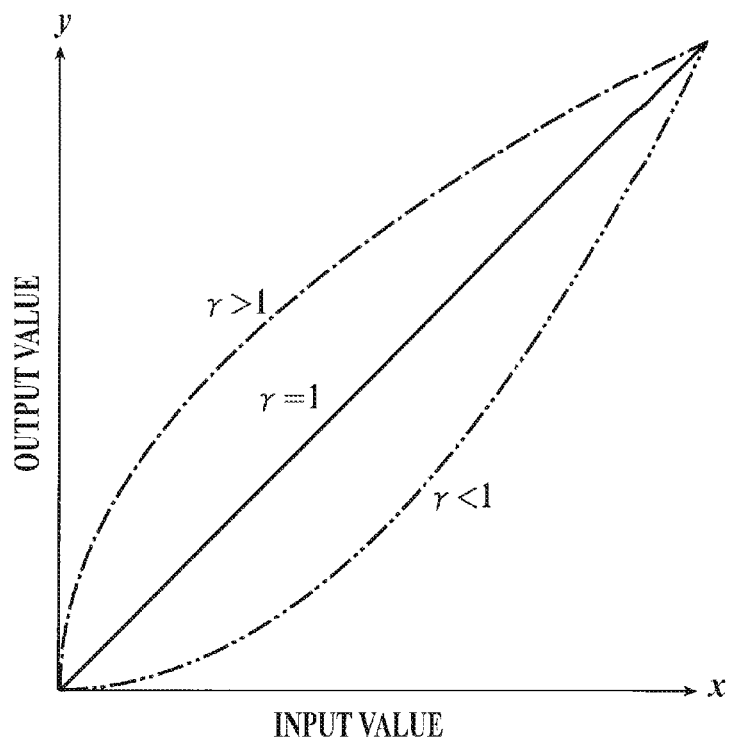
FIG. 23 is a diagram describing coefficient of gamma conversion.
Figure 24B:
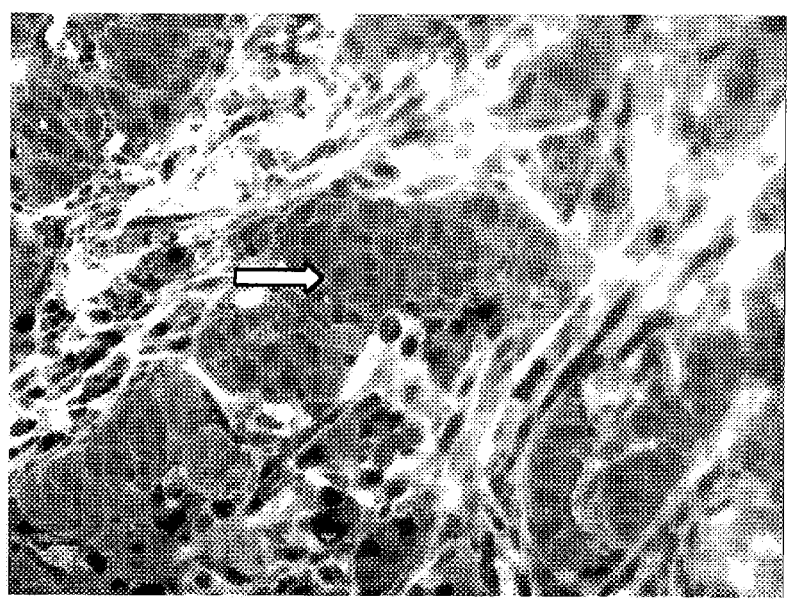
FIG. 24B is a diagram showing the fluorescent image shown in FIG. 24A after gamma conversion.

Gamma conversion converts the value of each pixel by the formula of [formula 1]. The asterisk in the [formula 1] is a multiplication symbol. γ is a parameter showing a degree of a γ curve. As shown in FIG. 23, when γ>1, the γ curve is convex upward and when γ<1, the γ curve is convex downward. For example, when the density becomes higher as the pixel value shifts from small to large, gamma conversion is performed as γ<1, and in a case opposite of the above, gamma conversion is performed as γ>1. FIG. 24B shows a monochrome image after gamma conversion. Compared to the portion shown with an arrow in FIG. 24A, it is possible to understand that the contrast is enhanced and the shape of the cell nucleus becomes clear.

$$I\_after(x,y)=M*(I\_before(x,y)/M)^{1/\gamma} \quad \text{[Formula 1]}$$

I_before(x,y): DENSITY VALUE BEFORE CONVERSION
I_after(x,y): DENSITY VALUE AFTER CONVERSION

M: MAXIMUM DENSITY VALUE OF IMAGE (EXAMPLE: 255 IN 8 BIT IMAGE)

γ: PARAMETER SHOWING DECREE OF γ CURVE

Next, the threshold processing is performed on the monochrome image after contrast correction using the threshold determined in advance and each pixel is binarized (step S703). Further, noise processing (step S704), and labeling processing (step S705) are performed, and the image with the cell nucleus extracted (cell nucleus image) as shown in FIG. 14 is obtained. The processing in steps S703, S704, and S705 are the same as the steps S302, S303, and S304 of FIG. 12, respectively, and the description is to be referred.

After the labeling processing, the processing advances to step S15 of FIG. 20.

In step S14, the fluorescent bright point is extracted from the fluorescent image (step S14). The processing of step S14 is the same as the processing described using FIG. 15 in the first embodiment, and therefore the description is to be referred. After extracting the fluorescent bright point, the processing advances to step S15 of FIG. 20.

In step S15 of FIG. 20, analysis processing is performed based on information of the region of the extracted cell nucleus and the information of the fluorescent bright point, and the feature amount showing the expression amount of the specific protein in the ROI is calculated (step S15). The processing of step S15 is similar to the processing described using FIG. 18 in the first embodiment, and therefore the description is to be referred.

Next, the calculated feature amount is displayed on the display section 23 (step S16). In step S16, similar to the analysis result screen 231 shown in FIG. 19, an analysis result screen is displayed displaying the fluorescent image which is the source of the analysis and the feature amount obtained by analyzing the fluorescent image. A frame border showing the region of the specified ROI is displayed in the fluorescent image which is the source of the analysis. Moreover, a print button and a transmit button are provided in the analysis result screen and the analysis result can be printed or output to the external device.

As described above, when the HE staining is performed on the tissue slice with the staining by the predetermined fluorescent indicator material, even if only the fluorescent image is used, the feature amount showing the expression amount of the specific protein in the ROI can be calculated. In the fluorescent image, the shape of the cell including the cell nucleus and the fluorescent bright point showing the expression of a specific biological substance are both included in one image. Therefore, by displaying the fluorescent image with the feature amount, the physician is able to understand the shape of the cell of the tissue, the expression status of the specific protein and the feature amount at once without comparing the two images of the bright field image and the fluorescent image or matching the positions of the two images as in conventional methods.

As described above, according to the image processor 2A, when the ROI of the analysis target is specified on the operation section 22 from the cell shape image showing the shape of the cell in the tissue slice (bright field image or fluorescent image), the control section 21 extracts the region of the cell nucleus from the bright field image or the fluorescent image and also extracts the fluorescent bright point showing the expression of the specific protein from the fluorescent image. Then, the feature amount showing the expression amount of the specific protein in the specified ROI is calculated based on the region of the cell nucleus and the fluorescent bright point in the ROI specified on the operation section 22, and the feature amount is output.

Therefore, the feature amount showing the expression of the specific protein calculated based on the cell nucleus and the fluorescent bright point in the ROI can be provided to the physician, and the physician is able to quantitatively understand the expression amount of the specific protein in a desired region. Therefore, the prognostic expectation and determining the future treatment plan becomes easier.

Here, as described above, overexpression of the specific protein such as the HER2 protein can be seen in the cell membrane of the cell with cancer. Therefore, the number of fluorescent bright points for each one of the cell in the ROI showing the expression amount of the specific protein for each one of the cell nucleus in the ROI can be said to be a feature amount quantitatively showing the degree of malignity of the cancer of the cell in the ROI. Therefore, quantitative information for prognostic expectation and determining the future treatment plan can be provided to the physician by output of the number of fluorescent bright points for each one of the cell in the ROI as the feature amount.

Moreover, when the feature amount is output, the synthesis image of the cell shape image and the fluorescent image with the annotation showing the position of the ROI overlapped on the image is output. Therefore, it is possible to easily understand the state such as the distribution and the size of the cell in the ROI and the expression status of the specific protein.

Moreover, according to the image processor 2A of the second embodiment, the feature amount showing the expression amount of the specific protein in the ROI is calculated and output using one fluorescent image showing the shape of the cell of the tissue slice as well as the expression of the specific protein in the tissue slice as the fluorescent bright point. Therefore, accurate feature amount can be calculated without synthesizing a plurality of images or performing processing of matching the position. Since the fluorescent image is displayed on the display section 23, the physician is easily able to understand both the cell nucleus and the expression of the protein from one image.

The description in the above embodiments are suitable examples of the present invention, and the present invention is not limited to the above.

For example, according to the first and second embodiments, HER2 protein in breast cancer is described as the example of the specific protein, however, the protein is not limited to the above. By changing the biological substance recognition site when the fluorescent image is obtained according to the type of lesion (cancer) which is to be the target of diagnosis, it is possible to provide the physician with the feature amount quantitatively showing the expression amount of the specific protein according to the type of lesion.

The above description discloses an example which uses an HDD, a semiconductor nonvolatile memory, or the like as the computer readable medium of the program of the present invention, however, the present invention is not limited to the above. A portable recording medium such as a CD-ROM, etc. can be applied as other computer readable media. A carrier wave can be applied as the medium which provides the data of the program of the present invention through a communication line.

The detailed configuration and the detailed operation of each device composing the pathological diagnosis assistance system 100 can be suitably changed within the scope of the present invention.

The entire disclosure of Japanese Patent Application No. 2012-078717 filed on Mar. 30, 2012 including description, claims, drawings, and abstract are incorporated herein by reference in its entirety.

INDUSTRIAL APPLICABILITY

The present invention can be used in the field of medicine as a medical image processor which processes a microscopic image of a tissue slice.

DESCRIPTION OF REFERENCE NUMERALS 100 pathological diagnosis assistance system
1A microscopic image obtaining apparatus
2A image processor
21 control section
22 operation section
23 display section
24 communication I/F
25 storage section
26 bus
3A cable

The invention claimed is:

1. A medical image processor comprising:
an input unit to input a cell shape image showing a shape of a cell in a tissue slice and a fluorescent image showing expression of a specific protein in the tissue slice as a fluorescent bright spot, the fluorescent image being obtained using a fluorescent substance included nanoparticle, which has an average particle diameter in the range including 30 nm to 800 nm;
an operation unit to specify an analysis target region from the cell shape image;
a cell nucleus extracting unit which extracts a region of a cell nucleus from the cell shape image;
a fluorescent bright point extracting unit which extracts a fluorescent bright point showing expression of the specific protein from the fluorescent image;
a feature amount calculating unit which calculates a feature amount showing an expression amount of the specific protein in the specified analysis target region based on the extracted cell nucleus region in the analysis target region specified with the operation unit and the fluorescent bright point; and
an output unit which outputs the calculated feature amount,
wherein the florescent substance included nanoparticle is a nanoparticle with a fluorescent substance dispersed inside, the feature amount calculating unit obtains information of a number of fluorescent bright points and a number of cell nuclei in the analysis target region specified with the operation unit, and based on the obtained number of cell nuclei and the number of fluorescent bright points, the feature amount calculating unit calculates the feature amount showing the expression amount of the specific protein in the specified analysis target region, and the feature amount calculating unit calculates a number of the fluorescent bright points in each cell nucleus in the specified analysis target region as the feature amount showing the expression amount of the specific protein, and
wherein the florescent bright point extracting unit extracts the fluorescent bright spot showing expression of the specific protein from the fluorescent image using an immunohistochemical (IHC) method.

2. The medical image processor of claim 1,
further comprising, a synthesis image unit which generates a synthesis image of the cell shape image and the fluorescent image,
wherein, the output unit outputs the synthesis image overlapped with an annotation showing a position of the analysis target region specified with the operation unit together with the feature amount.

3. The medical image processor of claim 1, wherein,
the cell shape image and the fluorescent image are combined to form one synthetic image which shows the shape of the cell in the tissue slice and the expression of the specific protein in the tissue slice as the fluorescent bright point.

4. The medical image processor of claim 1, wherein the fluorescent substance is a quantum dot.

5. A non-transitory computer-readable storage medium including a program for controlling a computer to function as:
an input unit to input a cell shape image showing a shape of a cell in a tissue slice and a fluorescent image showing expression of a specific protein in the tissue slice as a fluorescent bright point, the fluorescent image being obtained using a fluorescent substance included nanoparticle, which has an average particle diameter in the range including 30 nm to 800 nm;
an operation unit to specify an analysis target region from the cell shape image;
a cell nucleus extracting unit which extracts a region of a cell nucleus from the cell shape image;
a fluorescent bright point extracting unit which extracts a fluorescent bright point showing expression of the specific protein from the fluorescent image;
a feature amount calculating unit which calculates a feature amount showing an expression amount of the specific protein in the specified analysis target region based on the extracted cell nucleus region in the analysis target region specified with the operation unit and the fluorescent bright point; and
an output unit which outputs the calculated feature amount,
wherein the fluorescent substance included nanoparticle is a nanoparticle with a fluorescent substance dispersed inside, the feature amount calculating unit obtains information of a number of fluorescent bright points and a number of cell nuclei in the analysis target region specified with the operation unit, and based on the obtained number of cell nuclei and the number of fluorescent bright points, the feature amount calculating unit calculates the feature amount showing the expression amount of the specific protein in the specified analysis target region, and the feature amount calculating unit calculates a number of the fluorescent bright points in each cell nucleus in the specified analysis target region as the feature amount showing the expression amount of the specfic protein, and
wherein the fluorescent bright point extracting unit extracts the fluorescent bright spot showing expression of the specific protein from the fluorescent image using an immunohistochemical (IHC) method.

6. The non-transitory computer-readable storage medium of claim 5, wherein the fluorescent substance is a quantum dot.

* * * * *